(12) United States Patent
Thalladi et al.

(10) Patent No.: US 8,883,135 B2
(45) Date of Patent: Nov. 11, 2014

(54) CRYSTALLINE FORM OF A PYRIDYL-PIPERAZINYL HEPATITIS C VIRUS INHIBITOR

(71) Applicants: Venkat R. Thalladi, Foster City, CA (US); Jerry Nzerem, South San Francisco, CA (US); Xiaojun Huang, Sunnyvale, CA (US); Weijiang Zhang, Concord, CA (US)

(72) Inventors: Venkat R. Thalladi, Foster City, CA (US); Jerry Nzerem, South San Francisco, CA (US); Xiaojun Huang, Sunnyvale, CA (US); Weijiang Zhang, Concord, CA (US)

(73) Assignee: Theravance Biopharma R&D IP, LLC, South San Francisco, CA (US)

( * ) Notice: Subject to any disclaimer, the term of this patent is extended or adjusted under 35 U.S.C. 154(b) by 0 days.

(21) Appl. No.: 13/870,244

(22) Filed: Apr. 25, 2013

(65) Prior Publication Data

US 2013/0295048 A1  Nov. 7, 2013

Related U.S. Application Data

(60) Provisional application No. 61/772,124, filed on Mar. 4, 2013, provisional application No. 61/641,991, filed on May 3, 2012.

(51) Int. Cl.
| | |
|---|---|
| *A61K 45/06* | (2006.01) |
| *A61K 31/496* | (2006.01) |
| *C07D 401/14* | (2006.01) |
| *C07D 403/14* | (2006.01) |

(52) U.S. Cl.
CPC ............ *C07D 401/14* (2013.01); *C07D 403/14* (2013.01); *A61K 45/06* (2013.01); *A61K 31/496* (2013.01)
USPC ........ 424/85.4; 514/254.05; 514/43; 544/370

(58) Field of Classification Search
USPC ................ 424/85.4; 514/254.05, 43; 544/370
See application file for complete search history.

(56) References Cited

U.S. PATENT DOCUMENTS

| | | |
|---|---|---|
| 2008/0050336 A1 | 2/2008 | Bachand et al. |
| 2010/0215618 A1 | 8/2010 | Carter et al. |
| 2012/0114600 A1 | 5/2012 | McKinnell et al. |

FOREIGN PATENT DOCUMENTS

| | | |
|---|---|---|
| WO | 2010/094977 A1 | 8/2010 |

OTHER PUBLICATIONS

International Search Report for PCT/US2013/038132 dated Jul. 3, 2013.

*Primary Examiner* — Melenie McCormick
*Assistant Examiner* — Kathrien Cruz
(74) *Attorney, Agent, or Firm* — Jeffrey A. Hagenah; Roberta P. Saxon

(57) ABSTRACT

The invention provides crystalline solid forms of (((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester. The invention also provides pharmaceutical compositions comprising such crystalline solid forms, methods of using such crystalline solid forms to treat hepatitis C virus infection, and processes useful for preparing such crystalline solid forms.

27 Claims, 6 Drawing Sheets

CRYSTALLINE FORM OF A PYRIDYL-PIPERAZINYL HEPATITIS C VIRUS INHIBITOR

CROSS-REFERENCE TO RELATED APPLICATIONS

This application claims the benefit of U.S. Provisional Application Nos. 61/641,991, filed on May 3, 2012 and 61/772,124, filed on Mar. 4, 2013, the disclosures of which are incorporated herein by reference in their entirety.

BACKGROUND OF THE INVENTION

1. Field of the Invention

The invention is directed to crystalline forms of a pyridyl-piperazinyl compound which are useful as hepatitis C virus inhibitors. The invention is also directed to pharmaceutical compositions comprising such crystalline compounds, methods of using such compounds to treat HCV infection, and processes and intermediates useful for preparing such compounds.

2. State of the Art

Recent estimates place the number of people infected with the hepatitis C virus (HCV) worldwide at more than 170 million, including 3 million people in the United States. The infection rate is thought to be roughly 4 to 5 times that of the human immunodeficiency virus (HIV). While in some individuals, the natural immune response is able to overcome the virus, in the majority of cases, a chronic infection is established, leading to increased risk of developing cirrhosis of the liver and hepatocellular carcinomas. Infection with hepatitis C, therefore, presents a serious public health problem.

The virus responsible for HCV infection has been identified as a positive-strand RNA virus belonging to the family Flaviviridae. The HCV genome encodes a polyprotein that during the viral lifecycle is cleaved into ten individual proteins, including both structural and non-structural proteins. The six non-structural proteins, denoted as NS2, NS3, NS4A, NS4B, NS5A, and NS5B have been shown to be required for RNA replication. In particular, the NS5A protein appears to play a significant role in viral replication, as well as in modulation of the physiology of the host cell. Effects of NS5A on interferon signaling, regulation of cell growth and apoptosis have also been identified. (Macdonald et al., *Journal of General Virology* (2004), 85, 2485-2502.) Compounds which inhibit the function of the NS5A protein are expected to provide a useful approach to HCV therapy.

Commonly-assigned U.S. Provisional Application Nos. 61/410,267, filed on Nov. 4, 2010, 61/444,046, filed on Feb. 17, 2011, and 61/492,267, filed on Jun. 1, 2011, and U.S. application Ser. No. 13/288,216, filed on Nov. 3, 2012 disclose pyridyl-piperazinyl compounds. In particular, the compound ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (compound 1):

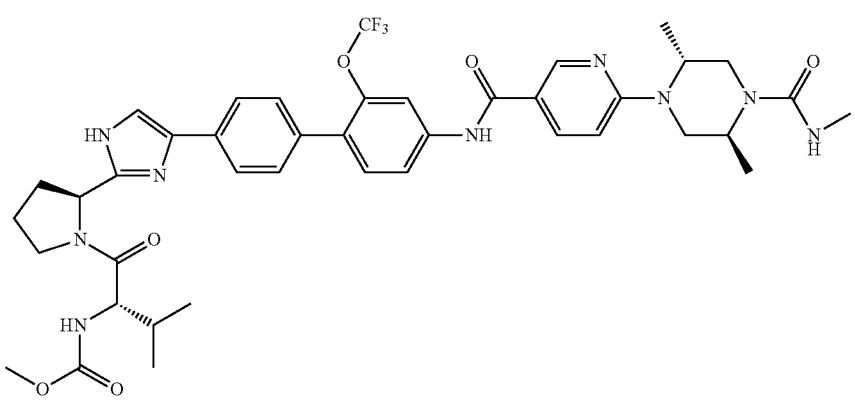

is specifically disclosed in these applications as an inhibitor of the hepatitis C virus.

To effectively use this compound as a therapeutic agent, it would be desirable to have a solid-state form that can be readily manufactured and that has acceptable chemical and physical stability. For example, it would be highly desirable to have a physical form that is thermally stable, for example at temperatures exceeding about 230° C. or about 260° C. and is not deliquescent, thereby facilitating processing and storage of the material. Crystalline solids are generally preferred over amorphous forms, for enhancing purity and stability of the manufactured product. However, the formation of crystalline forms of organic compounds is highly unpredictable. No reliable methods exist for predicting which, if any, form of an organic compound will be crystalline. Moreover, no methods exist for predicting which, if any, crystalline form will have the physically properties desired for use as pharmaceutical agents.

No crystalline forms of compound 1 have previously been reported. Accordingly, a need exists for a stable, non-deliquescent crystalline form of compound 1 which has an acceptable level of hygroscopicity and a high melting point.

SUMMARY OF THE INVENTION

The present invention provides crystalline solid forms of ((S)-1-{(S)-2-[4-(4'-{[6-((2R,5S)-2,5-dimethyl-4-methyl-carbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (1) and of the dihydrochloride salt thereof in both anhydrous and monohydrate forms.

Surprisingly, crystalline compound 1 has been found to exhibit no significant thermal events below a temperature of about 260° C. and to exhibit a weight change of about 3% when exposed to a range of relative humidity between about 2% and about 90% at room temperature. Furthermore, neither crystalline compound 1 nor the anhydrous and hydrate forms of the crystalline dihydrochloride salt of compound 1 is deliquescent when exposed to up to about 90% relative humidity at room temperature.

Among other uses, the crystalline solid forms of the invention are expected to be useful for preparing pharmaceutical compositions for treating hepatitis C virus infections. Accordingly, in another of its composition aspects, the invention provides a pharmaceutical composition comprising a pharmaceutically-acceptable carrier and crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester or the crystalline dihydrochloride salt or crystalline monohydrate dihydrochloride salt thereof.

In addition, the invention provides a pharmaceutical composition comprising a crystalline form of the invention, a pharmaceutically-acceptable carrier and one or more other therapeutic agents useful for treating hepatitis C viral infections.

The invention also provides a method of treating a hepatitis C viral infection in a mammal, the method comprising administering to the mammal a therapeutically effective amount of a crystalline form or of a pharmaceutical composition of the invention. In addition, the invention provides a method of treating a hepatitis C viral infection in a mammal, the method comprising administering to the mammal a crystalline form or a pharmaceutical composition of the invention and one or more other therapeutic agents useful for treating hepatitis C viral infections. Further, the invention provides a method of inhibiting replication of the hepatitis C virus in a mammal, the method comprising administering a crystalline form or a pharmaceutical composition of the invention.

The invention also provides a crystalline form of the invention as described herein for use in medical therapy, as well as the use of a crystalline form of the invention in the manufacture of a formulation or medicament for treating a hepatitis C viral infection in a mammal.

BRIEF DESCRIPTION OF THE DRAWINGS

Various aspects of the present invention are illustrated by reference to the accompanying drawings.

DETAILED DESCRIPTION OF THE INVENTION

Figure 1:
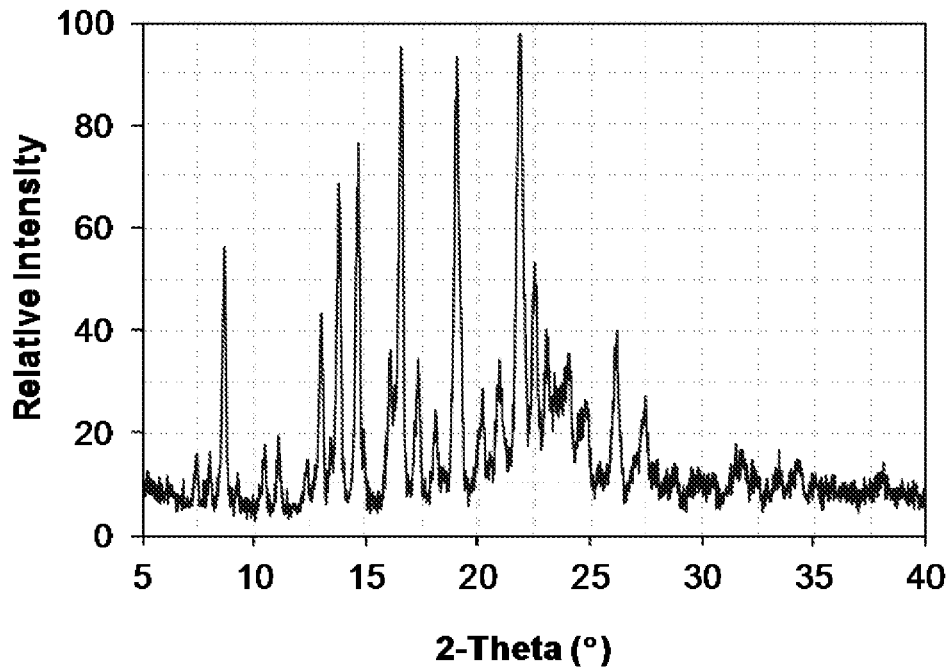
FIG. 1 shows a powder x-ray diffraction (PXPD) pattern of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

The invention provides a crystalline solid form of ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (1) and of the dihydrochloride salt thereof in both anhydrous and monohydrate forms.

Compound 1 and intermediates thereto have been named according to the IUPAC conventions as implemented in the AutoNom feature of the commercially-available (MDL® ISIS/Draw software (Symyx, Santa Clara, Calif.).

Compound 1 has multiple chiral centers. However, it will be understood that minor amounts of other stereoisomers may also be present unless otherwise indicated, provided that the utility of the depicted or named compound is not eliminated by the presence of another stereoisomer.

Definitions

When describing the compounds, compositions and methods of the invention, the following terms have the following meanings, unless otherwise indicated.

The term "therapeutically effective amount" means an amount sufficient to effect treatment when administered to a patient in need of treatment.

The term "treatment" as used herein means the treatment of a disease, disorder, or medical condition in a patient (such as hepatitis C viral infection), such as a mammal (particularly a human) which includes one or more of the following:

(a) preventing the disease, disorder, or medical condition from occurring, i.e., preventing the reoccurrence of the disease or medical condition or prophylactic treatment of a patient that is pre-disposed to the disease or medical condition;

(b) ameliorating the disease, disorder, or medical condition, i.e., eliminating or causing regression of the disease, disorder, or medical condition in a patient, including counteracting the effects of other therapeutic agents;

(c) suppressing the disease, disorder, or medical condition, i.e., slowing or arresting the development of the disease, disorder, or medical condition in a patient; or (d) alleviating the symptoms of the disease, disorder, or medical condition in a patient.

Representative Crystalline Forms of the Invention

In one aspect, the invention provides crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (1)

In one aspect, crystalline compound 1 is characterized by a powder x-ray diffraction (PXRD) pattern having significant diffraction peaks, among other peaks, at 2θ values of 8.68±0.20, 13.78±0.20, 14.68±0.20, 16.56±0.20, and 19.08±0.20.

As is well known in the field of powder x-ray diffraction, peak positions of PXRD spectra are relatively less sensitive to experimental details, such as details of sample preparation and instrument geometry, than are the relative peak heights. In another aspect, crystalline compound 1 is characterized by an x-ray powder diffraction pattern in which the peak positions are substantially in accordance with those shown in FIG. 1.

In another aspect, crystalline compound 1 is characterized by its behavior when exposed to high temperature. As demonstrated in FIG. 2, the differential scanning calorimetry (DSC) trace exhibits a melting endotherm between about 270° C. and about 275° C. The onset of melting is observed at about 266° C. and the melting peak is at about 273° C. Melting is closely followed by decomposition. A shallow endotherm is observed in the range 25-100° C. The low temperature feature may correspond to surface-adsorbed moisture or solvent adhered to the particles or it may correspond to moisture included in the lattice. No other thermal events were observed prior to the melting transition.

Figure 3:
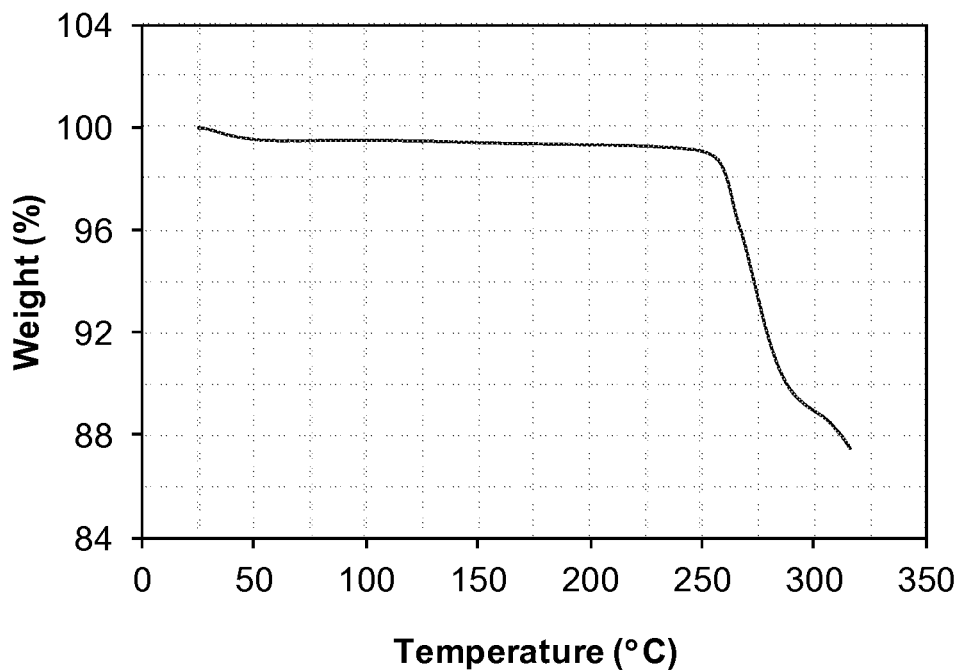
FIG. 3 shows a thermal gravimetric analysis (TGA) plot of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester.

The thermal gravimetric analysis (TGA) trace of FIG. 3 shows a modest weight loss at temperatures corresponding to the shallow endotherm in the DSC thermogram. No other weight loss is observed until temperatures above the melting temperature. The compound decomposes after melting, as seen by significant weight loss at temperatures above about 275° C.

Figure 4:
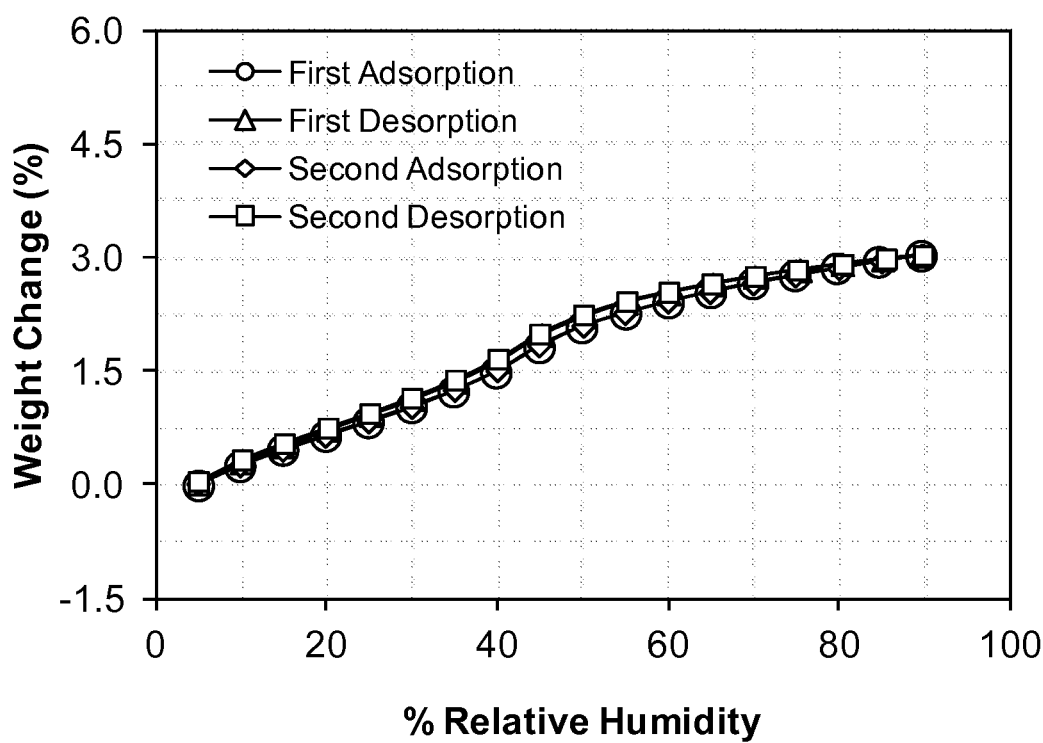
FIG. 4 shows a dynamic moisture sorption (DMS) isotherm of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester.

Crystalline compound 1 has been demonstrated to have a reversible sorption/desorption profile with a small propensity for hygroscopicity. Crystalline compound 1 has demonstrated a weight gain of about 3% or less in the humidity range of 2% to 90% relative humidity at room temperature, as shown in FIG. 4. No hysteresis was observed in two cycles and the resultant solid showed the same powder diffraction pattern as the starting material, indicating no change in form during the experiment.

In another aspect, the invention provides the crystalline dihydrochloride salt of compound 1 in anhydrous form. The anhydrous dihydrochloride salt of compound 1 contains between about 1.8 and about 2.2 molar equivalents of chloride ions per mole of compound 1, including between about 1.9 and about 2.1 molar equivalents of chloride ions per mole of compound 1. In one aspect, the anhydrous dihydrochloride salt of compound 1 contains about 2 molar equivalents of chloride ions per mole of compound 1, The crystalline anhydrous dihydrochloride salt is identified by the PXRD pattern of FIG. 5, the DSC profile of FIG. 6, and the TGA plot of FIG. 7. In one aspect, crystalline anhydrous dihydrochloride salt is characterized by a powder x-ray diffraction (PXRD) pattern having diffraction peaks at 2θ values of 8.87±0.20, 13.49±0.20, 14.30±0.20, 16.40±0.20, 19.13±0.20, 20.63±0.20, 21.38±0.20, and 21.95±0.20. In another aspect, the crystalline anhydrous dihydrochloride salt is characterized by a diffraction pattern in which the peak positions are substantially in accordance with those shown in FIG. 5.

Figure 6:
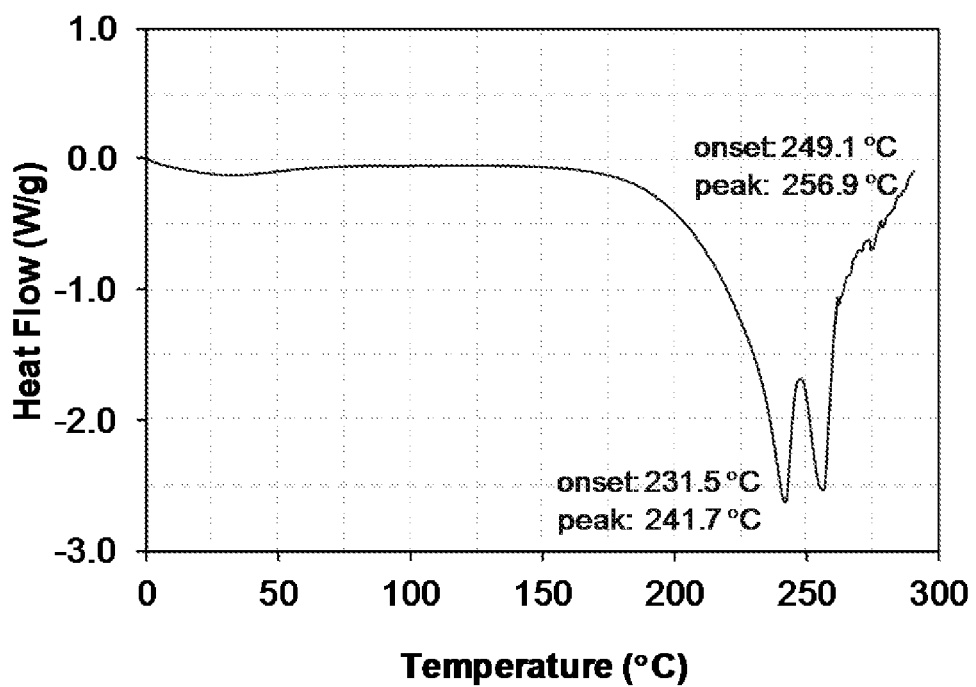
FIG. 6 shows a differential scanning calorimetry (DSC) thermogram of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride anhydrous form.
Figure 7:
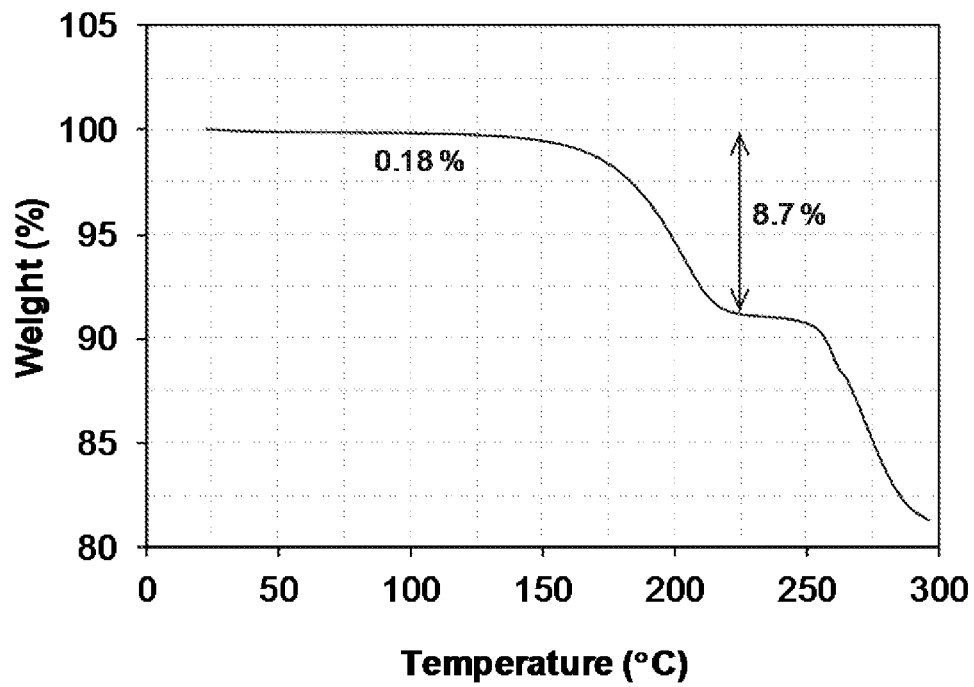
FIG. 7 shows a thermal gravimetric analysis (TGA) plot of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride anhydrous form.

The DSC profile of FIG. 6 shows two peaks in endothermic heat flow between about 230° C. and about 260° C. The thermal behavior of the anhydrous dihydrochloride salt exhibited in FIGS. 6 and 7 is consistent with a melting transition at about 242° C. associated with a loss of two equivalents of HCl. A clear step-like weight loss of 8.7% is observed in the TGA at about the temperature of the melting transition, which may be compared with the theoretical weight loss for two equivalents of HCl of 8.2%. The second endotherm in the DSC, consistent with the significant weight loss after about 250° C. in the TGA, most likely corresponds to the melting of the freebase. The early loss of mass of less than 0.2 weight percent in the 20-100° C. range in the TGA, corresponding to the shallow endotherm in the DSC thermogram, most likely corresponds to the loss of surface adsorbed moisture or solvent.

The crystalline anhydrous dihydrochloride salt of compound 1 has been demonstrated to have a reversible sorption/desorption profile with a small propensity for hygroscopicity.

Figure 8:
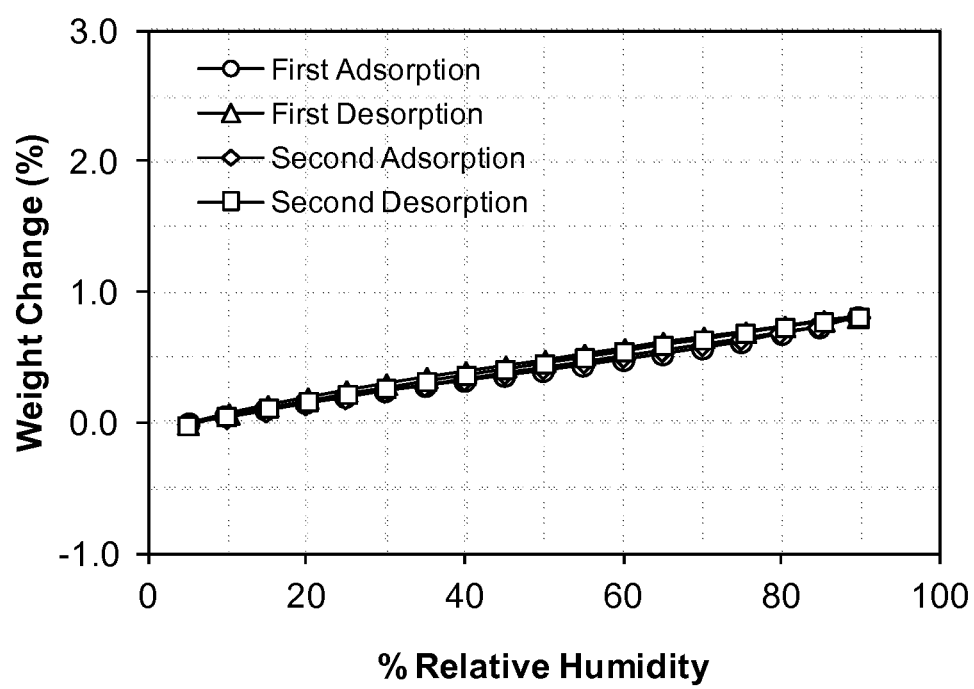
FIG. 8 shows a dynamic moisture sorption (DMS) isotherm of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride anhydrous form.

The anhydrous dihydrochloride salt has demonstrated a weight gain of about 0.8% in the humidity range of 2% to 90% relative humidity at room temperature, as shown in FIG. 8. No hysteresis was observed in two cycles and the resultant solid showed the same powder diffraction pattern as the starting material, indicating no change in form during the experiment.

In yet another aspect, the invention provides a crystalline dihydrochloride salt of compound 1 in monohydrate form. The monohydrate form comprises between about 0.8 and about 1.2 molar equivalents of water per mole of dihydrochloride salt of compound 1, including between about 0.9 and about 1.1 molar equivalents of water per mole of dihydrochloride salt. The chloride ion content of the monohydrate form is similar to that of the anhydrous form. The monohydrate form of the dihydrochloride salt contains between about 1.8 and about 2.2 molar equivalents of chloride ions per mole of compound 1, including between about 1.9 and about 2.1 molar equivalents of chloride ions per mole of compound 1, and about 2 molar equivalent of chloride ions per mole of compound 1.

In one aspect, a crystalline monohydrate dihydrochloride salt of the present invention is characterized by a powder x-ray diffraction (PXRD) pattern having diffraction peaks, at 2θ values of 9.11±0.20, 10.22±0.20, 13.70±0.20, 14.60±0.20, 18.32±0.20, 19.85±0.20, 20.33±0.20, and 21.80±0.20. In another aspect, a crystalline monohydrate dihydrochloride salt of compound 1 is characterized by a powder x-ray diffraction pattern in which the peak positions are substantially in accordance with those shown in FIG. 9.

Figure 10:
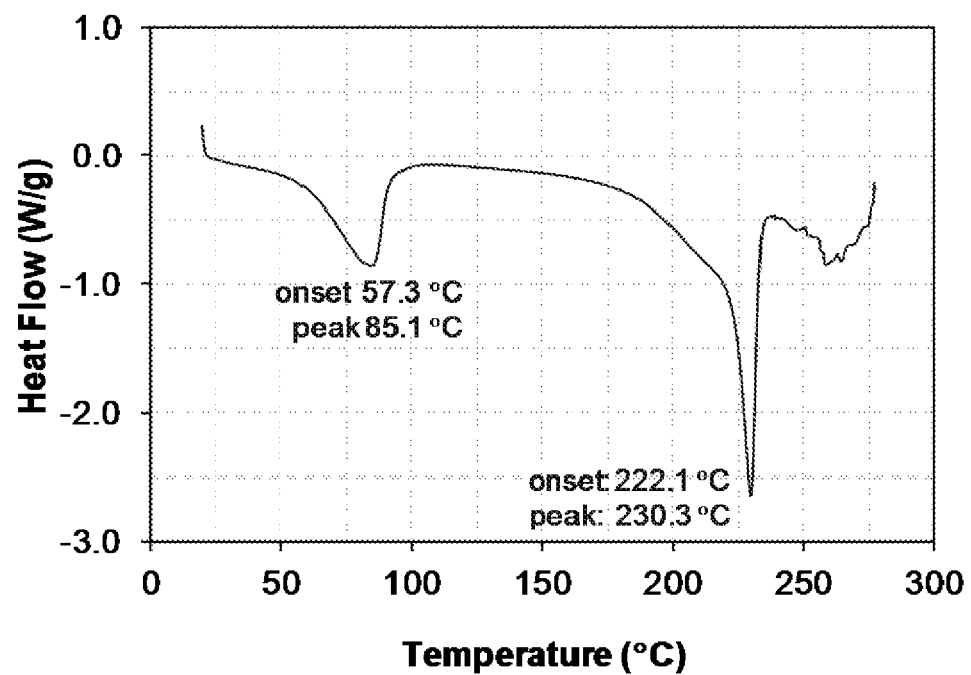
FIG. 10 shows a differential scanning calorimetry (DSC) thermogram of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride monohydrate form.

The crystalline monohydrate is also characterized by its differential scanning calorimetry (DSC) trace of FIG. 10 which exhibits an endotherm spanning about 30° C. to about 100° C., which is believed to correspond to the loss of one equivalent of water, with a local maximum in endothermic heat flow between about 55° C. and about 95° C. The DSC trace also exhibits a melting endotherm between about 225° C. and about 235° C. with a peak at about 230° C. Melting is associated with loss of two equivalents of HCl. The interpretation of the DSC trace is consistent with the TGA plot of FIG. 11 which shows an early mass loss of 2.2 weight percent in the range of about 20° C. to about 100° C. corresponding to the loss of one equivalent of lattice-bound water, as compared with the theoretical value of 1.98%, and the loss of a small amount of surface-bound moisture or solvent. As in the anhydrous form, the step-like loss of 8.87 weight percent at the melting transition most likely corresponds to the loss of two equivalents of HCl. Decomposition occurring during and after melting appears to partially coincide with the loss of HCl.

Figure 12:
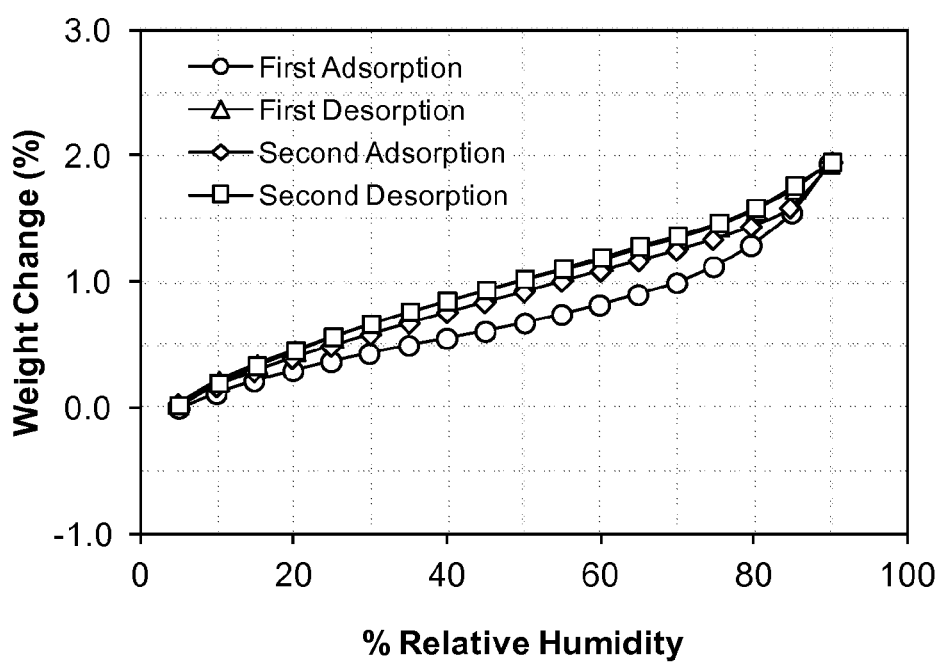
FIG. 12 shows a dynamic moisture sorption (DMS) isotherm of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride monohydrate form.

The sorption/desorption profile of the monohydrate form is shown in FIG. 12, which shows a weight gain of about 2% at 90% relative humidity during the initial adsorption segment. The particles lose all the adsorbed moisture during the desorption segment and revert to the initial stage. The second cycle of adsorption and desorption coincides with the first desorption segment. The solid remaining after two cycles showed the same PXRD pattern as the starting material, indicating no change in form during the experiment.

These properties of the crystalline forms of this invention are further illustrated in the Examples below.

Synthetic Procedures and Intermediates

Compound 1, ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester can be prepared from readily available starting materials in solid amorphous form using the procedures described in the Examples below, or using the procedures described in the commonly-assigned U.S. application listed in the Background section of this application.

In one method of preparation, crystalline compound 1 is prepared by dissolving amorphous compound 1 in a polar diluent to form a crystallization process mixture. The process mixture can be sonicated using conventional equipment to facilitate dissolution and crystallization. Typically, the process mixture is held for two or more days at ambient temperature. Suitable diluents for this reaction include ethanol, methanol or isopropanol in combination with acetone, dichloromethane, acetonitrile, ethyl acetate, toluene, or p-xylene. Upon completion of the reaction, crystalline compound 1 is isolated from the process mixture by any conventional means, such as filtration, concentration, centrifugation, and the like.

The process of preparing a crystalline form of the invention can optionally include the use of a seed crystal to produce predominately a particular crystalline form. Typically seed crystals are prepared by slow crystallization without stirring and without applying cooling, as described, for example, above.

In another method of preparation, crystalline compound 1 is advantageously prepared directly from the crude product of the final step of the synthesis of compound 1, illustrated in the following scheme, without purification of the amorphous form.

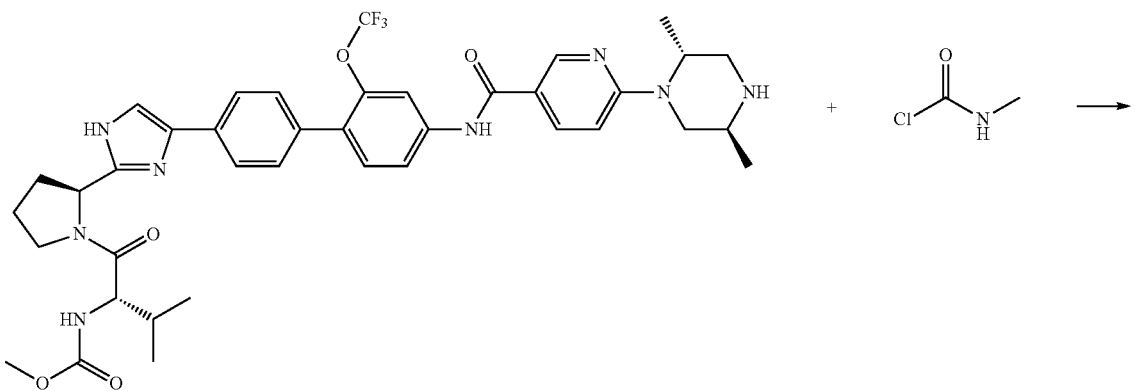

-continued

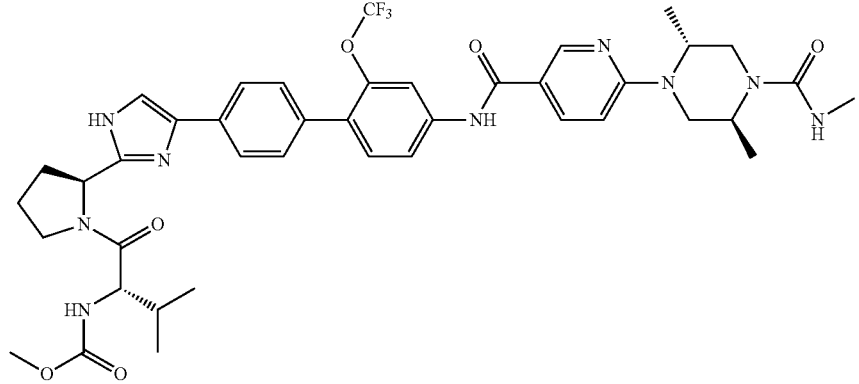

As described in Example 3 below, ((S)-1-{(S)-2-[4-(4'-{[6-((2R,5S)-2,5-dimethyl-piperazin-1-yl)-pyridine-3-carbonyl}-amino]-2'-trifluoromethoxy-biphenyl-4-yl)-1H-imidazol-2-yl]-pyrrolidine-1-carbonyl}-2-methyl-propyl)-carbamic acid methyl ester (2) is reacted with methylaminoformyl chloride to provide a crude product, which is recovered by conventional extraction and drying. The reaction is typically performed in the presence of an excess of base, in an inert diluent such as dichloromethane. Next, methanol is added to the crude product followed by the slow addition of water in a ratio of methanol:water of about 2.5:1 to about 2.7:1 to form a crystallization mixture. Seeds of crystalline compound 1 are added about halfway through the water addition. The crystallization mixture is stirred for a period of several days to form crystalline compound 1. To increase purity, the product can be recrystallized by a similar process: the crystalline compound is dissolved in methanol, water and seeds are added, such that the ratio of methanol to water in the mixture is about 2.5:1, and the mixture is stirred for a period of at least 12 hours to provide crystalline compound 1, which is recovered conventionally.

Accordingly, in a method aspect, among other processes, the invention provides a process for preparing crystalline compound 1, the process comprising: (a) dissolving amorphous compound 1 in a polar diluent selected from ethanol, methanol or isopropanol in combination with acetone, dichloromethane, acetonitrile, ethyl acetate, toluene, or p-xylene to provide a crystallization solution and (b) allowing the solution to evaporate to provide crystalline compound 1.

In an additional method aspect, the invention provides a process for preparing crystalline compound 1, the process comprising (a) dissolving the crude product of the reaction of 2 with methylaminoformyl chloride in methanol, (b) adding water and seeds of crystalline compound 1, such that the ratio of methanol to water is between about 2.5:1 and about 2.7:1 to form a reaction mixture; and (c) stirring the reaction mixture until crystalline compound 1 is formed. Optionally, the method can include a recrystallization step comprising: (a) dissolving the crystalline product in methanol, (b) adding water and seeds of crystalline compound 1, such that the ratio of methanol to water is about 2.5:1 to form a reaction mixture; and (c) stirring the reaction mixture until crystalline compound 1 is formed.

The anhydrous crystalline dihydrochloride salt of compound 1 may be prepared by dissolving amorphous dihydrochloride salt of compound 1 in a polar diluent, for example an ethanol-acetone mixture and stirring the solution in a closed vial for at least two days at ambient temperature. Resulting crystalline material can be isolated by conventional means. Optionally, seed crystals obtained in an earlier run can be added to facilitate crystallization.

A process for preparing the crystalline dihydrochloride monohydrate form starts with a slurry of the amorphous dihydrochloride salt of compound 1. Typically, the amorphous dihydrochloride salt is dissolved in ethanol, or ethanol, water and acetone, with heating, and stirred until a thick slurry is formed from which the crystalline dihydrochloride monohydrate form is isolated by conventional means.

Pharmaceutical Compositions

The solid forms of the invention are typically used in the form of a pharmaceutical composition or formulation. Such pharmaceutical compositions may be administered to a patient by any acceptable route of administration including, but not limited to, oral, rectal, vaginal, nasal, inhaled, topical (including transdermal) and parenteral modes of administration.

Accordingly, in one of its compositions aspects, the invention is directed to a pharmaceutical composition comprising a pharmaceutically-acceptable carrier or excipient and a solid form of the invention. Optionally, such pharmaceutical compositions may contain other therapeutic and/or formulating agents if desired. When discussing compositions and uses thereof, the "solid form of the invention" may also be referred to herein as the "active agent".

The pharmaceutical compositions of the invention typically contain a therapeutically effective amount of a solid form of the present invention. Those skilled in the art will recognize, however, that a pharmaceutical composition may contain more than a therapeutically effective amount, i.e., bulk compositions, or less than a therapeutically effective amount, i.e., individual unit doses designed for multiple administration to achieve a therapeutically effective amount.

Typically, such pharmaceutical compositions will contain from about 0.1 to about 95% by weight of the active agent; preferably, from about 5 to about 70% by weight; and more preferably from about 10 to about 60% by weight of the active agent.

Any conventional carrier or excipient may be used in the pharmaceutical compositions of the invention. The choice of a particular carrier or excipient, or combinations of carriers or excipients, will depend on the mode of administration being used to treat a particular patient or type of medical condition or disease state. In this regard, the preparation of a suitable pharmaceutical composition for a particular mode of administration is well within the scope of those skilled in the pharmaceutical arts. Additionally, the carriers or excipients used in the pharmaceutical compositions of this invention are commercially-available. By way of further illustration, conventional formulation techniques are described in Remington: The Science and Practice of Pharmacy, 20th Edition, Lippincott Williams & White, Baltimore, Md. (2000); and H. C. Ansel et al., Pharmaceutical Dosage Forms and Drug Delivery Systems, 7th Edition, Lippincott Williams & White, Baltimore, Md. (1999).

Representative examples of materials which can serve as pharmaceutically acceptable carriers include, but are not limited to, the following: sugars, such as lactose, glucose and sucrose; starches, such as corn starch and potato starch; cellulose, such as microcrystalline cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical compositions.

Pharmaceutical compositions are typically prepared by thoroughly and intimately mixing or blending the active agent with a pharmaceutically-acceptable carrier and one or more optional ingredients. The resulting uniformly blended mixture can then be shaped or loaded into tablets, capsules, pills and the like using conventional procedures and equipment.

The pharmaceutical compositions of the invention are preferably packaged in a unit dosage form. The term "unit dosage form" refers to a physically discrete unit suitable for dosing a patient, i.e., each unit containing a predetermined quantity of active agent calculated to produce the desired therapeutic effect either alone or in combination with one or more additional units. For example, such unit dosage forms may be capsules, tablets, pills, and the like, or unit packages suitable for parenteral administration.

In one embodiment, the pharmaceutical compositions of the invention are suitable for oral administration. Suitable pharmaceutical compositions for oral administration may be in the form of capsules, tablets, pills, lozenges, cachets, dragees, powders, granules; or as a solution or a suspension in an aqueous or non-aqueous liquid; or as an oil-in-water or water-in-oil liquid emulsion; or as an elixir or syrup; and the like; each containing a predetermined amount of a compound of the present invention as an active ingredient.

When intended for oral administration in a solid dosage form (i.e., as capsules, tablets, pills and the like), the pharmaceutical compositions of the invention will typically comprise the active agent and one or more pharmaceutically-acceptable carriers, such as sodium citrate or dicalcium phosphate. Optionally or alternatively, such solid dosage forms may also comprise: fillers or extenders, such as starches, microcrystalline cellulose, lactose, sucrose, glucose, mannitol, and/or silicic acid; binders, such as carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and/or sodium carbonate; solution retarding agents, such as paraffin; absorption accelerators, such as quaternary ammonium compounds; wetting agents, such as cetyl alcohol and/or glycerol monostearate; absorbents, such as kaolin and/or bentonite clay; lubricants, such as talc, calcium stearate, magnesium stearate, solid polyethylene glycols, sodium lauryl sulfate, and/or mixtures thereof; coloring agents; and buffering agents.

Release agents, wetting agents, coating agents, sweetening, flavoring and perfuming agents, preservatives and anti-oxidants can also be present in the pharmaceutical compositions of the invention. Examples of pharmaceutically-acceptable antioxidants include: water-soluble antioxidants, such as ascorbic acid, cysteine hydrochloride, sodium bisulfate, sodium metabisulfate, sodium sulfite and the like; oil-soluble antioxidants, such as ascorbyl palmitate, butylated hydroxyanisole, butylated hydroxytoluene, lecithin, propyl gallate, alpha-tocopherol, and the like; and metal-chelating agents, such as citric acid, ethylenediamine tetraacetic acid, sorbitol, tartaric acid, phosphoric acid, and the like. Coating agents for tablets, capsules, pills and like, include those used for enteric coatings, such as cellulose acetate phthalate, polyvinyl acetate phthalate, hydroxypropyl methylcellulose phthalate, methacrylic acid methacrylic acid ester copolymers, cellulose acetate trimellitate, carboxymethyl ethyl cellulose, hydroxypropyl methyl cellulose acetate succinate, and the like.

Pharmaceutical compositions of the invention may also be formulated to provide slow or controlled release of the active agent using, by way of example, hydroxypropyl methyl cellulose in varying proportions; or other polymer matrices, liposomes and/or microspheres. In addition, the pharmaceutical compositions of the invention may optionally contain opacifying agents and may be formulated so that they release the active ingredient only, or preferentially, in a certain portion of the gastrointestinal tract, optionally, in a delayed manner. Examples of embedding compositions which can be used include polymeric substances and waxes. The active agent can also be in micro-encapsulated form, if appropriate, with one or more of the above-described excipients.

Suitable liquid dosage forms for oral administration include, by way of illustration, pharmaceutically-acceptable emulsions, microemulsions, solutions, suspensions, syrups and elixirs. Liquid dosage forms typically comprise the active agent and an inert diluent, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (esp., cottonseed, groundnut, corn, germ, olive, castor and sesame oils), glycerol, tetrahydrofuryl alcohol, polyethylene glycols and fatty acid esters of sorbitan, and mixtures thereof. Suspensions, in addition to the active ingredient, may contain suspending agents such as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

The solid forms of this invention can also be administered parenterally (e.g. by intravenous, subcutaneous, intramuscular or intraperitoneal injection). For parenteral administration, the active agent is typically admixed with a suitable vehicle for parenteral administration including, by way of example, sterile aqueous solutions, saline, low molecular weight alcohols such as propylene glycol, polyethylene glycol, vegetable oils, gelatin, fatty acid esters such as ethyl oleate, and the like. Parenteral formulations may also contain one or more anti-oxidants, solubilizers, stabilizers, preservatives, wetting agents, emulsifiers, buffering agents, or dispersing agents. These formulations may be rendered sterile by use of a sterile injectable medium, a sterilizing agent, filtration, irradiation, or heat.

Alternatively, the pharmaceutical compositions of the invention are formulated for administration by inhalation. Suitable pharmaceutical compositions for administration by inhalation will typically be in the form of an aerosol or a powder. Such compositions are generally administered using well-known delivery devices, such as a metered-dose inhaler, a dry powder inhaler, a nebulizer or a similar delivery device.

When administered by inhalation using a pressurized container, the pharmaceutical compositions of the invention will typically comprise the active ingredient and a suitable propellant, such as dichlorodifluoromethane, trichlorofluoromethane, dichlorotetrafluoroethane, carbon dioxide or other suitable gas. Additionally, the pharmaceutical composition may be in the form of a capsule or cartridge (made, for example, from gelatin) comprising a compound of the invention and a powder suitable for use in a powder inhaler. Suitable powder bases include, by way of example, lactose or starch.

The solid forms of the invention can also be administered transdermally using known transdermal delivery systems and excipients. For example, the active agent can be admixed with permeation enhancers, such as propylene glycol, polyethylene glycol monolaurate, azacycloalkan-2-ones and the like, and incorporated into a patch or similar delivery system. Additional excipients including gelling agents, emulsifiers and buffers, may be used in such transdermal compositions if desired.

It will be understood that any solid form of the invention, (i.e. crystalline compound 1, crystalline dihydrochloride salt of compound 1 anhydrous form or crystalline dihydrochloride salt of compound 1 monohydrate form) that is suitable for the particular mode of administration, can be used in the pharmaceutical compositions discussed above.

Utility

The present compound, ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (1) has been shown to inhibit viral replication in HCV replicon assays and therefore the solid forms of the invention are expected to be useful for the treatment of hepatitis C viral infections.

In one aspect, therefore, the invention provides a method of inhibiting replication of the hepatitis C virus in a mammal (e.g., a human), the method comprising administering to the mammal a therapeutically-effective amount of a solid form of the invention or of a pharmaceutical composition comprising a pharmaceutically-acceptable carrier and a solid form of the invention.

The invention further provides a method of treating hepatitis C viral infections in a mammal (e.g., a human), the method comprising administering to the mammal a therapeutically-effective amount of compound of the invention or of a pharmaceutical composition comprising a pharmaceutically-acceptable carrier and a solid form of the invention.

The solid forms of the invention may inhibit viral replication by inhibiting the function of the NS5A protein encoded by the HCV genome. In one aspect, therefore, the invention provides a method of inhibiting the NS5A protein of HCV in a mammal, the method comprising administering to the mammal, a compound or a composition of the invention.

When used to treat HCV infections, the solid forms of the invention will typically be administered orally in a single daily dose or in multiple doses per day, although other forms of administration may be used. The amount of active agent administered per dose or the total amount administered per day will typically be determined by a physician, in the light of the relevant circumstances, including the condition to be treated, the chosen route of administration, the actual compound administered and its relative activity, the age, weight, and response of the individual patient, the severity of the patient's symptoms, and the like.

Suitable doses for treating HCV infections will range from about 1 to about 2000 mg/day of active agent, including from about 5 to about 300 mg/day and from about 10 to about 200 mg per day of active agent for an average 70 kg human.

Combination Therapy

Solid forms of the invention may also be used in combination with one or more agents which act by the same mechanism or by different mechanisms to effect treatment of HCV. Useful classes of agents for combination therapy include, but are not limited to, HCV NS3 protease inhibitors, HCV NS5B nucleoside and non-nucleoside polymerase inhibitors, helicase inhibitors, NS4B protein inhibitors, HCV viral entry inhibitors, cyclophyllin inhibitors, toll-like receptor agonists, inhibitors of heat shock proteins, interfering RNA, antisense RNA, HCV internal ribosome entry site (IRES) inhibitors, thiazolides, nucleoside analogs such as ribavirin and related compounds, interferons and other immunomodulatory agents, inosine 5'-monophosphate dehydrogenase (IMPDH) inhibitors, and other NS5A protein inhibitors. Agents which act to inhibit HCV replication by any other mechanism may also be used in combination with the present compounds.

HCV NS3 protease inhibitors which may be used in combination therapy include, but are not limited to, Incivek® (telaprevir, VX-950), boceprevir (SCH-503034), simeprevir (TMC-435), narlaprevir (SCH-900518), vaniprevir (MK-7009), danoprevir (ITMN-191, R-7227), BI-201335, ABT-450/r, asunaprevir (BMS-650032), GS-9256, GS-9451, sovaprevir (ACH-1625), ACH-2684, BMS-605339, VX-985, PHX-1766, BMS-791325, IDX-320, and MK-5172.

Examples of HCV NS5B nucleoside polymerase inhibitors include, but are not limited to, mericitabine (RG7128), IDX-184, sofosbuvir (GS-7977, PSI-7977), PSI-7851, PSI-938, BMS-986094 (INX-189, INX-08189), RG7348, MK-0608, TMC-649128, HCV-796, and ALS-2200 (VX-135), while, non-nucleoside HCV NS5B polymerase inhibitors, include but are not limited to, filibuvir (PF-8685540), tegobuvir (GS-9190), VX-222, VX-759, setrobuvir (ANA-598), ABT-072, ABT-333, BI-207127, BMS-791325, MK-3281, IDX-37, BMS-824393, TMC-647055.

A wide variety of interferons and pegylated interferons, including alpha, beta, omega, and gamma interferons, having antiviral, antiproliferative or immunomodulatory effects, can be combined with the present compounds. Representative examples include, but are not limited to, Intron® A (interferon-alpha2b), Actimmune® (interferon-gamma-1b), Alferon N, Advaferon®, Roferon-A (interferon alpha-2a) PegIntron® (peginterferon-alpha 2b), Alfaferone, Pegasys® (peginterferon alpha-2a), Alfanative (interferon alpha), Zalbin™ (albinterferon alpha-2b), Infergon® (interferon alfacon-1), Omega DUROS® (omega interferon), Locteron™ (interferon alpha), PEG-rIL-29 (pegylated interferon lambda), and Rebif® (interferon beta-1a).

Nucleoside analog antiviral agents include, but are not limited to, ribavirin (Copegus®, Rebetol®, Virazole®) and Viramidine (taribavirin). Interferons and ribavirin are also provided in the form of kits which include, for example, but are not limited to, Rebetron® (interferon alpha-2b/ribavirin) and Pegetron® (Peginterferon alpha-2b/ribavirin)

Useful compounds acting by other mechanisms include, but are not limited to: cyclophilin inhibitors, such as DEB-025, SCY-635, NIM-811, and cyclosporine and derivatives; toll-like receptor agonists, such as resiquimod, IMO-2125, and ANA-773, HCV viral entry inhibitors, such as civacir, thiazolides, such as nitazoxanide, and broad-spectrum viral inhibitors, such as, inosine-5'-monophosphate dehydrogenase (IMPDH) inhibitors.

In addition, compounds of the invention may be combined with an NS5A inhibitor, for example, daclatasvir (BMS-790052), AZD-7295, PPI-461, PPI-1301, GS-5885, GSK2336805, ABT-267, ACH-2928, ACH-3102, EDP-239, IDX-719, MK-8742, or PPI-668.

In another aspect, therefore, the invention provides a therapeutic combination for use in the treatment of hepatitis C viral infections, the combination comprising a solid form of the invention and one or more other therapeutic agents useful for treating HCV. For example, the invention provides a combination comprising a solid form of the invention and one or more agents selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin and related nucleoside analogs. Also provided, therefore, is a pharmaceutical composition comprising a solid form of the invention and one or more other therapeutic agents useful for treating HCV.

Further, in a method aspect, the invention provides a method of treating a hepatitis C viral infection in a mammal, the method comprising administering to the mammal a solid form of the invention and one or more other therapeutic agents useful for treating HCV.

In another method aspect, the invention provides a method of inhibiting replication of the hepatitis C virus in a mammal, the method comprising administering to the mammal a solid form of the invention and one or more other therapeutic agents useful for inhibiting replication of the hepatitis C virus.

For example, in one method aspect, the invention provides a method of treating a hepatitis C viral infection in a mammal, the method comprising administering to the mammal a solid form of the invention, an interferon or pegylated interferon, and ribavirin.

In another exemplary method aspect, the invention provides a method of treating a hepatitis C viral infection in a mammal, the method comprising administering to the mammal a solid form of the invention, an interferon or pegylated interferon, ribavirin, and an HCV NS3 protease inhibitor.

In still another method aspect, the invention provides a method of treating a hepatitis C viral infection in a mammal, the method comprising administering to the mammal a solid form of the invention, ribavirin, and an HCV NS3 protease inhibitor.

Still other all-oral combination therapies useful in other method aspects, include, for example, a solid form of the invention and an HCV NS3 protease inhibitor; a solid form of the invention and an HCV NS5B nucleoside polymerase inhibitor; a solid form of the invention, an HCV NS5B nucleoside polymerase inhibitor, and ribavirin; a solid form of the invention, an HCV NS3 protease inhibitor, and an HCV NS5B nucleoside polymerase inhibitor; a solid form of the invention, an HCV NS3 protease inhibitor, an HCV NS5B nucleoside polymerase inhibitor and ribavirin; a solid form of the invention, an HCV NS3 protease inhibitor, and an HCV NS5B non-nucleoside polymerase inhibitor; and a solid form of the invention, an HCV NS3 protease inhibitor, an HCV NS5B non-nucleoside polymerase inhibitor and ribavirin.

In another method aspect, the invention provides a method of inhibiting replication of the hepatitis C virus in a mammal, using a solid form of the invention in combination with other agents, as described above.

When used in combination therapy, the agents may be formulated in a single pharmaceutical composition, as disclosed above, or the agents may be provided in separate compositions that are administered simultaneously or at separate times, by the same or by different routes of administration. When administered separately, the agents are administered sufficiently close in time so as to provide a desired therapeutic effect. Such compositions can be packaged separately or may be packaged together as a kit. The two or more therapeutic agents in the kit may be administered by the same route of administration or by different routes of administration.

Compound 1 has been demonstrated to be a potent inhibitor of HCV replication in HCV replicon assays, as described in the following biological examples.

EXAMPLES

The following synthetic and biological examples are offered to illustrate the invention, and are not to be construed in any way as limiting the scope of the invention. In the examples below, the following abbreviations have the following meanings unless otherwise indicated. Abbreviations not defined below have their generally accepted meanings.

DCM=dichloromethane
DMSO=dimethyl sulfoxide
h=hour(s)
min=minute(s)
MTBE=methyl tert-butyl ether
RT=room temperature Reagents and solvents were purchased from commercial suppliers (Aldrich, Fluka, Sigma, etc.), and used without further purification. Reactions were run under nitrogen atmosphere, unless noted otherwise. Progress of reaction mixtures was monitored by thin layer chromatography (TLC), analytical high performance liquid chromatography (anal. HPLC), and mass spectrometry. Reaction mixtures were worked up as described specifically in each reaction; commonly they were purified by extraction and other purification methods such as temperature-, and solvent-dependent crystallization, and precipitation.

Analytical HPLC Method
Column: Zorbax Bonus-RP 3.5 μm. 4.6×150 mm
Column temperature: 35° C.
Flow rate: 1.0 mL/min
Mobile Phases: A=Water/ACN (98:2)+0.1% TFA
B=Water/ACN (10:90)+0.1% TFA,
Injection volume: 100-1500 μL
Detector wavelength: 214 nm
Sample preparation: Dissolve in 1:1 ACN:water
Gradient: 29 min total (time (min)/% B): 0.5/10, 24/90, 25/90, 26/10, 29/10

Preparation 1: (2S,5R)-4-[5-(4-Bromo-3-trifluoromethoxy-phenylcarbamoyl)-pyridin-2-yl]-2,5-dimethyl-piperazine-1-carboxylic acid tert-butyl ester (a) N-(4-Bromo-3-trifluoromethoxy-phenyl)-6-fluoro-nicotinamide

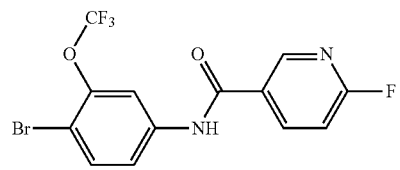 [SMILES: O=C(Nc1ccc(Br)c(OC(F)(F)F)c1)c1ccc(F)nc1]

To a solution of 4-bromo-3-trifluoromethoxy-phenylamine (3.15 g, 12.3 mmol) and triethylamine (3.43 mL, 24.6 mmol) in DCM (25 mL) was slowly added a solution of 2-fluoropyridine-5-carbonyl chloride (2.36 g, 14.8 mmol) in DCM (10 mL). After 2 h at RT, MTBE (90 mL) was added and the reaction mixture was washed with water, brine, and saturated sodium carbonate, dried, and evaporated to give a solid (5.4 g). Ethanol (43 mL) was added to the solid and then water (43 mL) was slowly added. The reaction mixture was stirred for 1.5 h, filtered, and washed with 1:4 ethanol:water (2×25 mL) to give the title intermediate as a white solid (3.87 g). Analytical HPLC: Retention time=21.3 min.

(b) (2S,5R)-4-[5-(4-Bromo-3-trifluoromethoxy-phenylcarbamoyl)-pyridin-2-yl]-2,5-dimethyl-piperazine-1-carboxylic acid tert-butyl ester

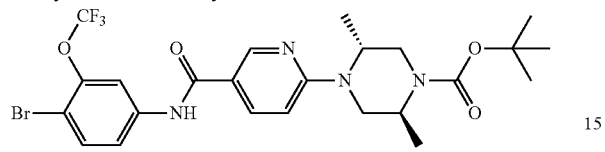

The product of the previous step (3.86 g, 10.2 mmol) (2S,5R)-2,5-dimethyl-piperazine-1-carboxylic acid tert-butyl ester (2.62 g, 12.2 mmol) and N,N-diisopropylethylamine (5.32 mL, 30.5) was dissolved in DMSO (12 mL). The reaction mixture heated at 120° C. for 3 h, diluted with EtOAc (100 mL), washed with water, and saturated $NH_4Cl$, water, and brine. The reaction mixture was evaporated to about 40% volume and 3 M HCl in cyclopentyl methyl ether (4.24 mL, 12.7 mmol) was added slowly. Seeds from a previous run at smaller scale were added and the reaction mixture was stirred for 2 days and filtered to provide the HCl salt of the title intermediate (5.15 g, 83% yield). Analytical HPLC: Retention time=21.1 min.

Preparation 2: (2S,5R)-4-[5-(4'-{2-[(S)-1-((S)-2-Methoxycarbonylamino-3-methyl-butyryl)-pyrrolidin-2-yl]-1H-imidazol-4-yl}-2-trifluoromethoxy-biphenyl-4-ylcarbamoyl)-pyridin-2-yl]-2,5-dimethyl-piperazine-1-carboxylic acid tert-butyl ester

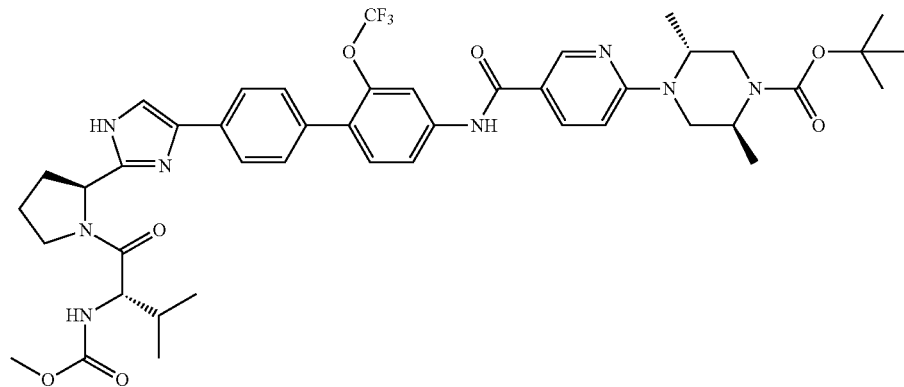 [SMILES: COC(=O)N[C@H](C(=O)N1CCC[C@H]1c1nc(-c2ccc(-c3ccc(NC(=O)c4ccc(N5C[C@H](C)N(C(=O)OC(C)(C)C)C[C@H]5C)nc4)cc3OC(F)(F)F)cc2)c[nH]1)C(C)C]

To a solution of ((S)-1-{(S)-2-[4-(4-bromo-phenyl)-1H-imidazol-2-yl]-pyrrolidine-1-carbonyl}-2-methyl-propyl)-carbamic acid methyl ester (3.05 g, 6.8 mmol), bis(pinacolato)diboron (1.81 g, 7.1 mmol) and potassium acetate (1.00 g, 10.2 mmol) was added nitrogen sparged toluene (15 mL). The resulting mixture was sparged with nitrogen and 1,1'-bis(diphenylphosphino)ferrocene-palladium(II)dichloride dichloromethane (Pd catalyst) (0.17 g, 0.204 mmol) was added. The reaction mixture was stirred at 90° C. overnight.

The reaction mixture was cooled to RT and to this mixture was added nitrogen sparged water (7.6 mL), potassium carbonate (5.16 g, 37.3 mmol), and (2S,5R)-4-[5-(4-bromo-3- trifluoromethoxy-phenylcarbamoyl)-pyridin-2-yl]-2,5-dimethyl-piperazine-1-carboxylic acid tert-butyl ester (4.35 g, 7.13 mmol). The reaction mixture was stirred at 95° C. overnight.

Another portion of the Pd catalyst used above (0.08 g, 0.10 mmol) was added to the reaction mixture. After 5 h, the reaction mixture was cooled to RT, diluted with EtOAc (150 mL), washed with water (150 mL) and brine (100 mL), dried over sodium sulfate, and evaporated to give a black residue (6.7 g), which was purified by silica gel chromatography (eluted with 50-100% EtOAc/hexane) to provide the title intermediate (5.3 g, 90% yield). Analytical HPLC: Retention time=14.7 min.

The reaction mixture was concentrated to dryness (124 g crude). Water 500 mL) was added and the mixture was extracted with EtOAc (2×500 mL). The aqueous layer was adjusted to pH 4 with 1:1 NaOH:water. Ethyl acetate (400 mL) and sat. aq. $Na_2CO_3$ (100 mL) were added and the layers were separated. The organic layer was dried over $Na_2SO_4$ and evaporated to give the title intermediate (62.8 g; 88% yield). Analytical HPLC: Retention time=10.0 min.

Example 1

Amorphous ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester Preparation 3: ((S)-1-{(S)-2-[4-(4'-{[6-((2R,5S)-2,5-Dimethyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester

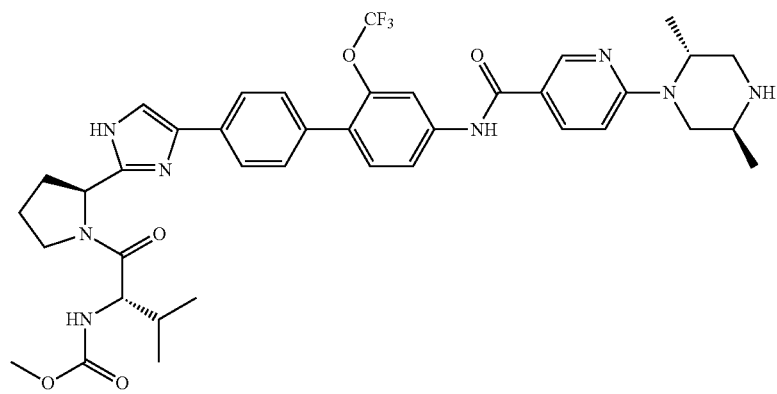

Acetyl chloride (63.2 mL, 888 mmol) was added to ethanol (360 mL) and stirred at RT for 1 h. To the resulting HCl solution was added a solution of (2S,5R)-4-[5-(4'-{2-[(S)-1-((S)-2-methoxycarbonylamino-3-methyl-butyryl)-pyrrolidin-2-yl]-1H-imidazol-4-yl}-2-trifluoromethoxy-biphenyl-4-ylcarbamoyl)-pyridin-2-yl]-2,5-dimethyl-piperazine-1-carboxylic acid tert-butyl ester (73 g, 84 mmol) in ethanol (360 mL). The reaction mixture was stirred at RT overnight.

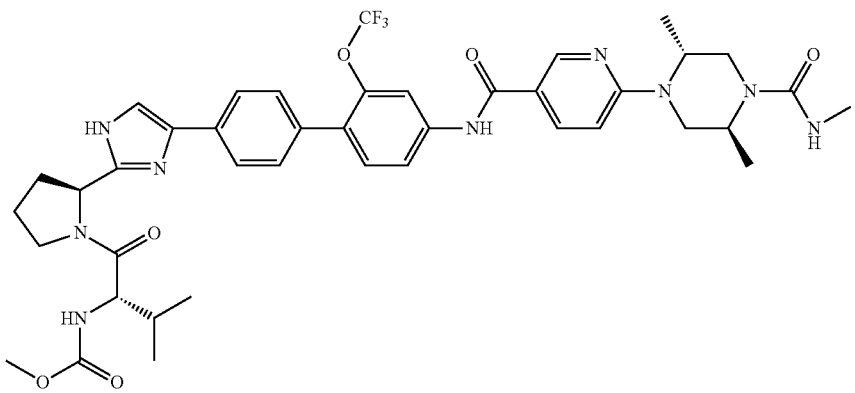

(a) ((S)-1-{(S)-2-[4-(4'-{[6-((2R,5S)-2,5-Dimethyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester tri-HCl Acetyl chloride (0.71 mL, 10.0 mmol) was added to ethanol (7 mL) and stirred at RT for 1 h. The resulting HCl solution was added to a solution of (2S,5R)-4-[5-(4'-{[S)-1-((S)-2-methoxycarbonylamino-3-methyl-butyryl)-pyrrolidin-2-yl]-1H-imidazol-4-yl}-2-trifluoromethoxy-biphenyl-4-ylcarbamoyl)-pyridin-2-yl]-2,5-dimethyl-piperazine-1-carboxylic acid tert-butyl ester (1.55 g, 1.8 mmol) in ethanol (7 mL). The reaction mixture was warmed to 35° C. and stirred overnight. The mixture was concentrated to dryness, and chased with DCM to provide the crude tri-HCl salt of the title intermediate (1.57 g) which was used directly in the next step. HPLC method C: Retention time=10.0 min.

(b) Amorphous ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester To a solution of the product of the previous step (1.57 g crude, ca. 1.80 mmol) and N,N-diisopropylethylamine (3.14 mL, 18.0 mmol) in DCM (24 mL) was slowly added 1 M methylaminoformyl chloride in DMA (1.8 mL). The reaction mixture stirred at RT for 1 h, and then 1 M methylaminoformyl chloride in DMA (1.8 mL) was added. The reaction was quenched with sat. aq. NaHCO₃ and the reaction mixture was stirred for 20 min. The layers were separated and the organic layer was dried and evaporated to give a residue. To the residue was added methanol (15 mL) followed by 2 N LiOH/water (3 mL). The reaction mixture was stirred at RT for 1 h, diluted with water, extracted with DCM (80 mL), dried, and evaporated to give a crude product which was purified by silica gel chromatography (40 g silica, 2-8% MeOH/DCM) to provide the title compound (0.93 g, 63% yield). Analytical HPLC: Retention time=11.0 min.

Example 2

Crystalline ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester In a 4 mL glass vial, ethanol (0.5 mL) was added to amorphous ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (21.6 mg) and the reaction mixture was vortexed and sonicated to dissolution. Acetone (0.5 mL) was added to the reaction solution and the reaction mixture was sonicated briefly. The solution was allowed to evaporate at ambient conditions in a loosely capped vial for two days to provide the title compound (18.2 mg).

Example 3

Crystalline ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester To a solution of ((S)-1-{(S)-2-[4-(4'-{[6-((2R,5S)-2,5-dimethyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (62.8 g, 74.1 mmol; Preparation 3) and N,N-diisopropylethylamine (20.1 mL, 115.2 mmol) in DCM (750 mL) was slowly added 1 M methylaminoformyl chloride in DMA (68.4 mL) over 10 min at 10-15° C. After 50 min, 1 M methylaminoformyl chloride in DMA (3.6 mL) was added and the reaction mixture was stirred overnight. To the reaction mixture was added water (750 mL) and 1 N HCl (40 mL). The organic layer was washed with water, dried over Na₂SO₄, and evaporated. Methanol (300 mL) and 2 N LiOH (10 mL) were added to the crude product and the reaction mixture was stirred for 30 min. Water (110 mL) was added slowly to the reaction mixture. Seeds of crystalline title product were added after 50 mL of water. The reaction mixture was stirred for 2 days and then methanol (60 mL) and water (24 mL) were added. After 30 min, the mixture was filtered. The solid was washed with 2:1 methanol:water (120 mL), and dried under vacuum at 35° C. overnight to provide the title compound (54 g).

The product of the previous step (54 g) was dissolved in methanol (550 mL) heated to 50° C. Activated charcoal (1.5 g) was added, the reaction mixture was stirred at 45-50° C. for 30 min and filtered. Water (220 mL) and seeds were added. The reaction mixture was stirred at RT overnight and filtered. The solid was washed with 2.5:1 methanol:water and dried under nitrogen for 5 h and then dried under vacuum at 30-35° C. overnight to give the title compound (46.5 g, 79% yield). Analytical HPLC: Retention time=11.1 min.

Example 4

Amorphous ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride Dichloromethane (100 mL) and methanol (50 mL) were added to ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (10.17 g, 12.40 mmol) and the solution was stirred for 10 min, then cooled to 3° C. and 3 M of HCl in cyclopentyl methyl ether (12.4 mL) was added dropwise keeping the temperature of the reaction mixture less than 10° C. The water bath was removed and the reaction mixture was stirred for 15 min, and concentrated to about 50 mL. Isopropyl acetate was added and the mixture was concentrated to dryness. The resulting material was vacuum dried at RT overnight and vacuum oven dried at RT over the weekend to provide the title compound (12.2 g).

Example 5

Crystalline ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride Anhydrous Form In a 20 mL glass vial, a 3:2 ethanol:acetone mixture (4 mL) was added to amorphous ((S)-1-{(S)-2-[4-(4'-{[6-((2R,5S)-2,5-dimethyl-4-methylcarbamoyl-piperazin-1-yl)-pyridine- 3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester diHCl (777 mg; Example 4) and the reaction mixture was vortexed and sonicated to dissolution. The resulting solution was allowed to evaporate over two days to yield an amorphous solid. Acetone (4 mL) and ethanol (0.1 mL) were then added to the solid, followed by sonication to provide a clear solution, which was stirred in a closed vial at RT for two days. The resulting crystalline solid was filtered and dried under vacuum for two hours. to provide the title compound (563 mg).

Example 6

Crystalline ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride Anhydrous Form Amorphous ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester diHCl (12 g) was dissolved in ethanol (120 mL) with stirring and then acetone (150 mL) was added drop-wise to the stirred solution until the solution became hazy. Seeds of crystalline title compound (product of Example 5) were added and the contents were stirred at RT for 18 h to yield a white slurry. Stirring was continued for an additional 48 h and the white to off-white solid was filtered, rinsed with ethyl acetate, and dried at RT under vacuum for 48 h to provide the title compound (7.88 g).

Example 7

Crystalline ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride Monohydrate Form Ethanol (2 mL) and acetone (15 mL) were added to amorphous ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester diHCl (1102 mg, Example 4). The reaction mixture was warmed to 60° C. and sonicated for 1 min to give a hazy solution. Ethanol (2 mL) was added to provide a clear solution, which was heated at 60° C. After about 5 mL of solvent had evaporated, acetone (10 mL) was added until the solution turned cloudy. The contents were stirred overnight to provide a crystalline slurry which was stirred for an additional 48 h and then allowed to settle. The supernatant solvents were decanted. To the remaining solid suspension was added water (0.5 mL) and dioxane (2 mL). The resulting mixture was filtered to give a white to off-white solid which was dried under vacuum for 12 h to provide the title compound (628 mg).

Example 8

Crystalline ((S)-1-{(S)-2-[4-(4'-{[6-((2R,5S)-2,5-Dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride Monohydrate Form Ethanol (2 mL), acetone (15 mL), 1 N HCl (0.3 mL), and deionized water (0.3 mL) were added to amorphous ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester diHCl (650 mg) and the reaction solution was stirred at 30° C. for 18 h to give a crystalline slurry and then stirred for 48 h at RT. The thickened slurry was filtered and air-dried for 2 h to provide the title compound (586 mg).

Examples 9-14

Properties of Solid Forms of the Invention

Samples of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (compound 1) prepared according to the process of Example 3 and of the crystalline dihydrochloride salt of compound 1 anhydrous form prepared in Example 6 were analyzed by x-ray powder diffraction (XRPD), differential scanning calorimetry (DSC), thermogravimetric analysis (TGA), and dynamic moisture sorption (DMS). A sample of the crystalline dihydrochloride salt of compound 1 monohydrate form prepared in Example 8 was analyzed by XRPD. The crystalline dihydrochloride salt of compound 1 monohydrate form prepared in Example 7 was analyzed by DSC, TGA, and DMS.

Example 10

X-Ray Powder Diffraction

Figure 5:
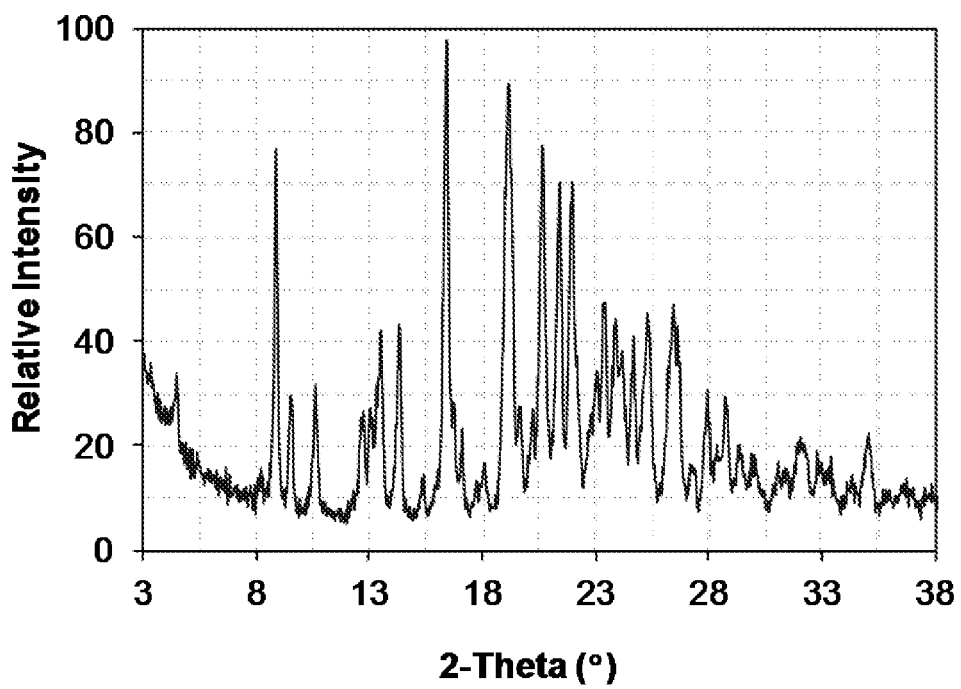
FIG. 5 shows a powder x-ray diffraction (PXPD) pattern of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride anhydrous form.
Figure 9:
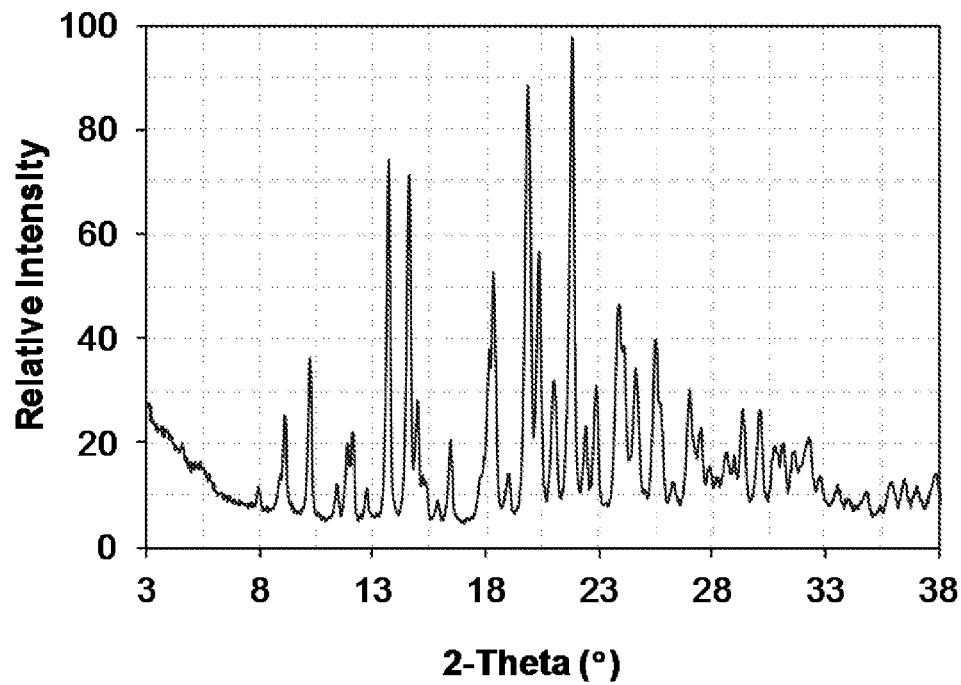
FIG. 9 shows a powder x-ray diffraction (PXPD) pattern of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride monohydrate form.

Powder X-ray diffraction patterns were obtained with a Thermo ARL X'Tra X-ray diffractometer using Cu—Kα radiation (λ=1.54051 Å) with output voltage of 45 kV and current of 40 mA. The instrument was operated in Bragg-Brentano geometry with incident, divergence, and scattering slits set to maximize the intensity at the sample. For measurement, a small amount of powder (5-25 mg) was gently pressed onto a sample holder to form a smooth surface and subjected to X-ray exposure. The samples were scanned in 2θ-2θ mode from 2° to 40° in 2θ with a step size of 0.03° and a scan speed of 2.0° per minute. The data acquisition was controlled by Thermo ARL measurement software (Version 1.2.0.0) and analyzed by Jade software (version 7.5.1). The instrument was calibrated with a quartz standard, within ±0.02° two-theta angle. Representative PXRD spectra of crystalline compound 1, crystalline dihydrochloride salt of compound 1 anhydrous form, and crystalline dihydrochloride salt of compound 1 monohydrate form are shown in FIGS. 1, 5, and 9, respectively. Observed PXRD two-theta peak positions and d-spacings for the above crystalline forms are shown in Tables 1, 2, and 3, respectively (only peaks having a relative peak height (H %) of about 20% or greater are listed).

TABLE 1

PXRD Data for Crystalline Compound 1

| 2-Theta | d(Å) | Height | H % |
|---|---|---|---|
| 8.68 | 10.18 | 235 | 56.9 |
| 13.00 | 6.81 | 163 | 39.4 |
| 13.78 | 6.42 | 282 | 68.2 |
| 14.68 | 6.03 | 327 | 79.3 |
| 16.08 | 5.51 | 132 | 32.0 |
| 16.56 | 5.35 | 413 | 100.0 |
| 17.32 | 5.12 | 113 | 27.3 |
| 19.08 | 4.65 | 392 | 95.0 |
| 20.96 | 4.24 | 96 | 23.4 |
| 21.90 | 4.06 | 381 | 92.3 |
| 22.56 | 3.94 | 156 | 37.8 |
| 23.06 | 3.85 | 84 | 20.5 |
| 24.06 | 3.70 | 113 | 27.5 |
| 26.22 | 3.40 | 144 | 34.9 |
| 27.50 | 3.24 | 83 | 20.1 |

TABLE 2

PXRD Data for Crystalline Dihydrochloride Salt of Compound 1 Anhydrous Form

| 2-Theta | d(Å) | Height | H % |
|---|---|---|---|
| 8.87 | 9.97 | 561 | 74.6 |
| 9.51 | 9.31 | 170 | 22.5 |
| 10.61 | 8.34 | 202 | 26.8 |
| 12.74 | 6.95 | 154 | 20.5 |
| 13.04 | 6.79 | 153 | 20.3 |
| 13.49 | 6.56 | 258 | 34.3 |
| 14.30 | 6.19 | 288 | 38.3 |
| 16.40 | 5.41 | 752 | 100.0 |
| 19.13 | 4.64 | 655 | 87.1 |
| 20.63 | 4.31 | 501 | 66.6 |
| 21.38 | 4.16 | 436 | 58.0 |
| 21.95 | 4.05 | 454 | 60.3 |
| 23.39 | 3.80 | 258 | 34.3 |
| 23.87 | 3.73 | 194 | 25.8 |
| 24.65 | 3.61 | 196 | 26.0 |
| 25.28 | 3.52 | 270 | 35.9 |
| 26.47 | 3.37 | 275 | 36.6 |
| 27.92 | 3.20 | 171 | 22.8 |

TABLE 3

PXRD Data for Crystalline Dihydrochloride Salt of Compound 1 Monohydrate Form

| 2-Theta | d(Å) | Height | H % |
|---|---|---|---|
| 9.11 | 9.70 | 174 | 19.4 |
| 10.22 | 8.65 | 312 | 34.7 |
| 13.70 | 6.47 | 711 | 79.1 |
| 14.60 | 6.07 | 617 | 68.7 |
| 18.14 | 4.89 | 195 | 21.7 |
| 18.32 | 4.84 | 479 | 53.3 |
| 19.85 | 4.47 | 751 | 83.6 |
| 20.33 | 4.37 | 505 | 56.2 |
| 20.99 | 4.23 | 238 | 26.5 |
| 21.80 | 4.08 | 899 | 100.0 |
| 22.85 | 3.89 | 222 | 24.7 |
| 23.90 | 3.72 | 317 | 35.2 |
| 24.59 | 3.62 | 214 | 23.8 |
| 25.46 | 3.50 | 321 | 35.7 |
| 25.70 | 3.47 | 200 | 22.3 |

Example 11

Thermal Analysis

Figure 2:
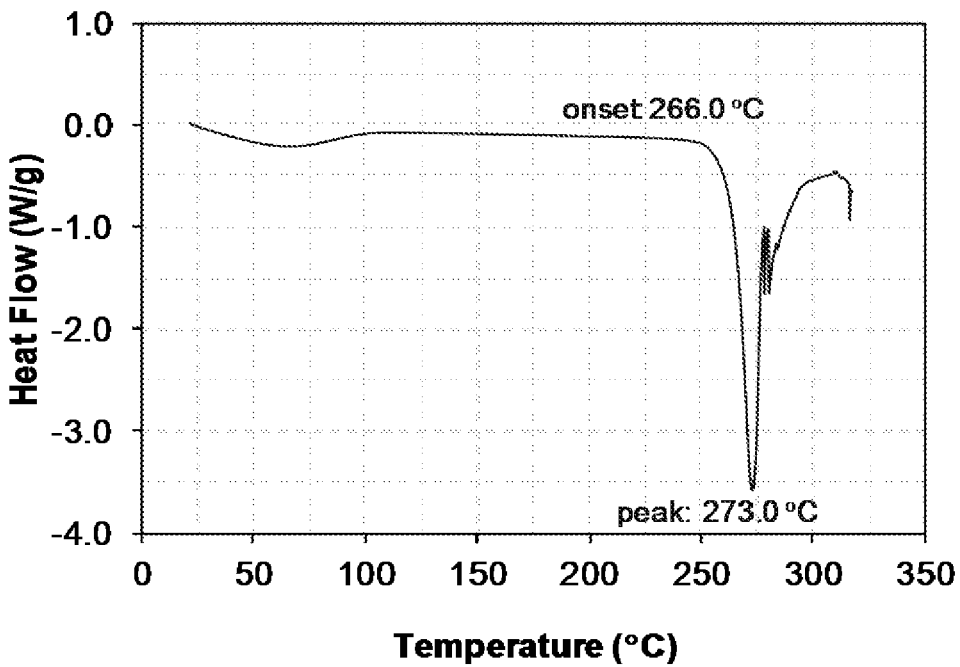
FIG. 2 shows a differential scanning calorimetry (DSC) thermogram of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester.

Differential scanning calorimetry (DSC) was performed using a TA Instruments Model Q-100 module with a Thermal Analyst controller. Data were collected and analyzed using TA Instruments Thermal Analysis software. A sample of each crystalline form was accurately weighed into a covered aluminum pan. After a 5 minute isothermal equilibration period at 5° C., the sample was heated using a linear heating ramp of 10° C./min from 0° C. to 200° C. Representative DSC thermograms of crystalline compound 1, crystalline dihydrochloride salt of compound 1 anhydrous form, and crystalline dihydrochloride salt of compound 1 monohydrate form are shown in FIGS. 2, 6, and 10, respectively.

Figure 11:
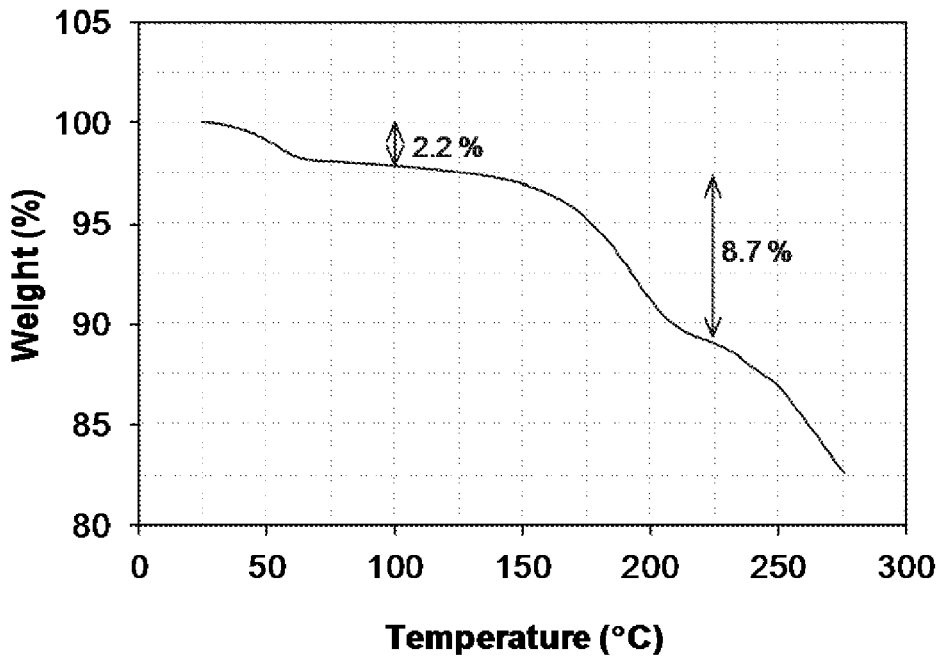
FIG. 11 shows a thermal gravimetric analysis (TGA) plot of crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester dihydrochloride monohydrate form.

Thermogravimetric analysis (TGA) measurements were performed using a TA Instruments Model Q-50 module equipped with high resolution capability. Data were collected using TA Instruments Thermal Analyst controller and analyzed using TA Instruments Universal Analysis software. A weighed sample was placed onto a platinum pan and scanned with a heating rate of 10° C. from ambient temperature to 200° C. The balance and furnace chambers were purged with nitrogen flow during use. Representative TGA traces crystalline compound 1, crystalline dihydrochloride salt of compound 1 anhydrous form, and crystalline dihydrochloride salt of compound 1 monohydrate form are shown in FIGS. 3, 7, and 11, respectively.

Example 12

Dynamic Moisture Sorption Assessment

Dynamic moisture sorption (DMS) measurements were performed for each crystalline form using a VTI atmospheric microbalance, SGA-100 system (VTI Corp., Hialeah, Fla. 33016). A weighed sample was used and the humidity was lowest possible value (close to 0% RH) at the start of the analysis. The DMS analysis consisted of two cycles with a scan rate of 5% RH/step over the full humidity range of 5% RH to 90% RH. The DMS run was performed isothermally at 25° C. Representative DMS traces for crystalline compound 1, crystalline dihydrochloride salt of compound 1 anhydrous form, and crystalline dihydrochloride salt of compound 1 monohydrate form are shown in FIGS. 4, 8, and 12, respectively.

Example 13

Determination of Chloride Ion Content

Chloride ion content of the crystalline dihydrochloride salt of compound 1 anhydrous form of Example 6 and of the crystalline dihydrochloride salt of compound 1 monohydrate form of Example 7 were analyzed by ion chromatography with conductivity detection using a Dionex ICS-2000 system. The anhydrous form was determined to have a chloride ion content of 7.6%, which may be compared with an expected value for a dihydrochloride salt of 7.94%. The monohydrate form was determined to have a chloride ion content of 7.6% which may be compared with an expected value of 7.78%.

Example 14

Determination of Water Content

The water content of the crystalline dihydrochloride salt of compound 1 monohydrate form of Example 7 was determined by the Karl Fischer method using a coulometric titrator to be 2.35%, which may be compared with an expected value for a monohydrate of 1.98%.

Biological Assays

The hepatitis C virus has been classified into six major different genotypes on the basis of nucleotide sequence, and further divided into subtypes within genotypes. Compounds of the invention demonstrated inhibition of HCV replication in one or more of the following HCV replicon assays.

Assay 1: HCV Genotype 1b Replicon Assay

The HCV genotype 1b replicon cell line was obtained from Apath LLC (Brooklyn, N.Y.) (APC144; Huh7 cell background). This subgenomic replicon contains the N-terminus of the HCV core protein fused to the neomycin-resistance selectable marker. The EMCV IRES lies downstream and drives expression of humanized *Renilla* luciferase fused to the non-structural proteins NS3-NS5B. This cell line was used to determine compound potency using the luciferase activity readout as a measurement of compound inhibition of replicon levels.

Cells were grown at 37° C. in a 5% $CO_2$ humidified incubator in DMEM (Invitrogen) with 10% FBS (HyClone), 1×NEAA (Invitrogen), 1× Pen-Strep (Invitrogen), and 500 μg/mL G418 (Invitrogen). On day 1 of the assay, cells were plated at 10,000 cells/well in white 96-well tissue culture plates (Costar) in 200 μL media lacking G418. Four hours later, once the cells have adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 hours. At the end of the incubation period, media and compound were removed from the plates and the luciferase activity was determined using Promega *Renilla*-Glo reagents.

To analyze the data, the luciferase activity was plotted vs. the compound concentration, and $EC_{50}$ values were determined from a 4-parameter robust fit model with the GraphPad Prism software package (GraphPad Software, Inc., San Diego, Calif.). Results are expressed as the negative decadic logarithm of the $EC_{50}$ value, $pEC_{50}$.

Test compounds having a higher $pEC_{50}$ value in this assay show greater inhibition of HCV genotype 1b replication. Compound 1 exhibited a $pEC_{50}$ value of at least 11 in this assay.

Assay 2: HCV Genotype 1a Replicon Assay

The HCV genotype 1a replicon cell line was obtained from Apath LLC (APC89; Huh7.5 cell background). This subgenomic replicon contains the N-terminus of the HCV core protein fused to the neomycin-resistance selectable marker. The EMCV IRES lies downstream and drives expression of the non-structural proteins NS3-NS5B. Compound potencies were determined using the NS3-specific protease activity in lysates as a measurement of compound inhibition of replicon levels.

Cells were grown at 37° C. in a 5% $CO_2$ humidified incubator in DMEM (Invitrogen) with 10% FBS (HyClone), 1×NEAA (Invitrogen), 1× Pen-Strep (Invitrogen), and 850 μg/mL G418 (Invitrogen). On day 1 of the assay, cells were plated at 15,000 cells/well in black 96-well tissue culture plates (Costar) in 200 μL media lacking G418. Four hours later, once the cells had adhered, the media was removed and replaced with media (no G418) containing dose-responses of test compounds. Compounds were initially diluted in DMSO and then diluted another 200× in media to bring the final DMSO concentration down to 0.5%. The cells were incubated with test compounds for 48 or 72 hours. At the end of the incubation period, media and compound were removed from the plates.

To determine the NS3-specific protease activity in lysates, the cells were lysed at room temperature in 50 μL/well of 50 mM Hepes pH 7.5, 150 mM NaCl, 15% Glycerol, 0.15% Triton X-100, 10 mM DTT for 20 minutes with shaking. 50 μL of an NS3/4a protease-specific FRET substrate (Anaspec RET S1 Cat#22991) was then added to the wells at a final concentration of 15 μM. The plates were incubated at 37° C. for 20 minutes, which corresponds to a timepoint at which the protease activity is still in the linear phase. Protease activity was determined by measuring fluorescence (Excitation: 340 nm; Emission: 509 nm).

To analyze the data, the fluorescence was plotted vs. the compound concentration, and EC50 values were determined from a 4-parameter robust fit model using GraphPad Prism software. Compound 1 exhibited a $pEC_{50}$ value of at least 10 in this assay.

Assay 3: Replicon Assays Against Resistant Mutants

To create replicon cells with resistant mutations of interest, the mutation was first introduced into the parental plasmid by site-directed mutagenesis. Mutations in genotype 1b included L31V and Y93H. Mutations in genotype 1a included Q30R and L31V. The replicon plasmid was then linearized and in vitro transcribed to RNA. The RNA was used to stably transfect Huh7 cells by electroporation, and new cell lines were selected with 500 μg/mL G418. Potencies of test compounds against these mutant cell lines were determined as previously described above for the HCV Genotype 1b and 1a replicon assays. Compound 1 exhibited a $pEC_{50}$ value of at least 8 in these assays.

Potencies of test compounds against additional mutations of interest were determined using transient transfection assays. These mutants included genotype 1a Y93H, M28T, and Q30E. The mutation was first introduced into the parental plasmid by site-directed mutagenesis. The replicon plasmid was then linearized and in vitro transcribed to RNA. The RNA was used to transiently transfect Huh-LUNET cells (obtained from ReBLikon GmbH, Schriesheim, Germany) by electroporation, and the potencies of test compounds against the mutants were determined as previously described. Compound 1 exhibited a $pEC_{50}$ value of at least 8 in these assays.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. Additionally, all publications, patents, and patent documents cited hereinabove are incorporated by reference herein in full, as though individually incorporated by reference.

What is claimed is:

1. A crystalline solid form of ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (compound 1) or a dihydrochloride salt thereof selected from:
   (a) crystalline compound 1 characterized by a powder x-ray diffraction pattern comprising diffraction peaks at 2θ values of 8.68±0.20, 13.78±0.20, 14.68±0.20, 16.56±0.20, and 19.08±0.20;

(b) crystalline dihydrochloride salt of compound 1 anhydrous form characterized by a powder x-ray diffraction pattern comprising diffraction peaks at 2θ values of 8.87±0.20, 13.49±0.20, 14.30±0.20, 16.40±0.20, 19.13±0.20, 20.63±0.20, 21.38±0.20, and 21.95±0.20; and (c) crystalline dihydrochloride salt of compound 1 monohydrate form characterized by a powder x-ray diffraction pattern comprising diffraction peaks at 2θ values of 9.11±0.20, 10.22±0.20, 13.70±0.20, 14.60±0.20, 18.32±0.20, 19.85±0.20, 20.33±0.20, and 21.80±0.20.

2. The crystalline solid form of claim 1, wherein the crystalline solid form is crystalline compound 1.

3. The crystalline solid form of claim 2, wherein the crystalline solid form is characterized by an x-ray powder diffraction pattern in which the peak positions are substantially in accordance with the peak positions of the pattern shown in FIG. 1.

4. The crystalline solid form of claim 2, wherein the crystalline solid form is characterized by a differential scanning calorimetry trace recorded at a heating rate of 10° C. per minute which shows a maximum in endothermic heat flow at a temperature between about 270° C. and about 275° C.

5. The crystalline solid form of claim 2, wherein the crystalline solid form is characterized by a differential scanning calorimetry trace substantially in accordance with that shown in FIG. 2.

6. The crystalline solid form of claim 1, wherein the crystalline solid form is a crystalline dihydrochloride salt of compound 1 anhydrous form.

7. The crystalline solid form of claim 6, wherein the crystalline solid form is characterized by an x-ray powder diffraction pattern in which the peak positions are substantially in accordance with the peak positions of the pattern shown in FIG. 5.

8. The crystalline solid form of claim 6, wherein the crystalline solid form is characterized by a differential scanning calorimetry trace recorded at a heating rate of 10° C. per minute which shows two peaks in endothermic heat flow at a temperature between about 230° C. and about 260° C.

9. The crystalline solid form of claim 6, wherein the crystalline solid form is characterized by a differential scanning calorimetry trace substantially in accordance with that shown in FIG. 6.

10. The crystalline solid form of claim 1, wherein the crystalline solid form is a crystalline dihydrochloride salt of compound 1 monohydrate form.

11. The crystalline solid form of claim 10, wherein the crystalline solid form is characterized by an x-ray powder diffraction pattern in which the peak positions are substantially in accordance with the peak positions of the pattern shown in FIG. 9.

12. The crystalline solid form of claim 10, wherein the crystalline solid form is characterized by a differential scanning calorimetry trace recorded at a heating rate of 10° C. per minute which shows a local maximum in endothermic heat flow at a temperature between about 55° C. and about 95° C. and a major peak in endothermic heat flow at a temperature between about 225° C. and about 235° C.

13. The crystalline solid form of claim 6, wherein the crystalline solid form is characterized by a differential scanning calorimetry trace substantially in accordance with that shown in FIG. 10.

14. A pharmaceutical composition comprising a crystalline solid form of claim 1 and a pharmaceutically-acceptable carrier.

15. The pharmaceutical composition of claim 14 further comprising one or more other therapeutic agents useful for treating hepatitis C viral infections.

16. The pharmaceutical composition of claim 15 wherein the one or more other therapeutic agents is selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin.

17. A method of treating hepatitis C viral infection in a mammal, the method comprising administering to the mammal a pharmaceutical composition comprising a compound of claim 1 and a pharmaceutically-acceptable carrier.

18. The method of claim 17 wherein the method further comprises administering one or more other therapeutic agents useful for treating hepatitis C viral infections.

19. The method of claim 18 wherein the one or more other therapeutic agents is selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin.

20. A method of inhibiting replication of the hepatitis C virus in a mammal, the method comprising administering to the mammal a pharmaceutical composition comprising a compound of claim 1 and a pharmaceutically-acceptable carrier.

21. The method of claim 20 wherein the method further comprises administering to the mammal one or more other therapeutic agents useful for inhibiting replication of the hepatitis C virus in a mammal.

22. The method of claim 21 wherein the one or more other therapeutic agents is selected from HCV NS3 protease inhibitors, HCV NS5B nucleoside and non-nucleoside polymerase inhibitors, interferons and pegylated interferons, cyclophilin inhibitors, HCV NS5A inhibitors, and ribavirin.

23. A process for preparing crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (compound 1), the process comprising:
(a) dissolving amorphous compound 1 in a polar diluent selected from ethanol, methanol or isopropanol in combination with acetone, dichloromethane, acetonitrile, ethyl acetate, toluene, or p-xylene to provide a crystallization solution; and
(b) allowing the solution to evaporate to provide crystalline compound 1.

24. A process for preparing crystalline ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (compound 1), the process comprising:
(a) dissolving the crude product of the reaction of ((S)-1-{(S)-2-[4-(4'-{[6-((2R,5S)-2,5-dimethyl-piperazin-1-yl)-pyridine-3-carbonyl}-amino]-2'-trifluoromethoxy-biphenyl-4-yl)-1H-imidazol-2-yl]-pyrrolidine-1-carbonyl}-2-methyl-propyl)-carbamic acid methyl ester with methylaminoformyl chloride in methanol,
(b) adding water and seeds of crystalline compound 1, such that the ratio of methanol to water is between about 2.5:1 and about 2.7:1 to form a reaction mixture; and
(c) stirring the reaction mixture until crystalline compound 1 is formed.

25. The process of claim 24 further comprising:
(d) dissolving the product of claim 24 step (c) in methanol,
(e) adding water and seeds of crystalline compound 1, such that the ratio of methanol to water is about 2.5:1 to form a reaction mixture; and
(f) stirring the reaction mixture until crystalline compound 1 is formed.

26. A process for preparing the crystalline dihydrochloride salt of ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (compound 1) anhydrous form, the process comprising:
(a) dissolving amorphous dihydrochloride salt of compound 1 in an ethanol-acetone mixture to form a solution; and
(b) stirring the solution in a closed vial at ambient temperature until the crystalline dihydrochloride salt of compound 1 is formed.

27. A process for preparing the crystalline dihydrochloride salt of ((S)-1-{(S)-2-[4-(4'-{[6-((2R,5S)-2,5-dimethyl-4-methylcarbamoyl-piperazin-1-yl)-pyridine-3-carbonyl]-amino}-2'-trifluoromethoxy-biphenyl-4-yl)-1H-imidazol-2-yl]-pyrrolidine-1-carbonyl}-2-methyl-propyl)-carbamic acid methyl ester (compound 1) monohydrate form, the process comprising:
(a) dissolving amorphous dihydrochloride salt of compound 1 in ethanol, or an ethanol, water and acetone mixture with heating to form a solution;
(b) stirring the solution until a thick slurry is formed; and
(c) isolating the crystalline dihydrochloride salt of compound 1 monohydrate form from the thick slurry.

* * * * *